(12) United States Patent
Das et al.

(10) Patent No.: US 8,916,361 B2
(45) Date of Patent: Dec. 23, 2014

(54) ELONGASE GENE AND USES THEREOF

(75) Inventors: Tapas Das, Worthington, OH (US);
Pradip Mukerji, Columbus, OH (US);
Padmavathy Krishnan, Hilliard, OH (US); Amanda E. Leonard, Columbus, OH (US); Suzette L. Pereira, Westerville, OH (US)

(73) Assignee: Abbott Laboratories, Abbott Park, IL (US)

( * ) Notice: Subject to any disclaimer, the term of this patent is extended or adjusted under 35 U.S.C. 154(b) by 661 days.

(21) Appl. No.: 11/939,641

(22) Filed: Nov. 14, 2007

(65) Prior Publication Data
US 2008/0214667 A1    Sep. 4, 2008

Related U.S. Application Data

(63) Continuation-in-part of application No. 11/601,544, filed on Nov. 17, 2006, now abandoned.

(51) Int. Cl.
| | | |
|---|---|---|
| *C12P 21/06* | (2006.01) | |
| *C12N 9/00* | (2006.01) | |
| *C12P 7/64* | (2006.01) | |
| *C12N 1/20* | (2006.01) | |
| *C12N 1/12* | (2006.01) | |
| *C12N 1/00* | (2006.01) | |
| *C12N 15/00* | (2006.01) | |
| *C12N 15/20* | (2006.01) | |
| *C07H 21/04* | (2006.01) | |
| *A01K 67/00* | (2006.01) | |
| *A01H 5/00* | (2006.01) | |
| *C12N 15/82* | (2006.01) | |
| *C12N 9/10* | (2006.01) | |

(52) U.S. Cl.
CPC .......... *C12N 9/1029* (2013.01); *C12N 15/8247* (2013.01)
USPC ..... 435/69.1; 435/183; 435/134; 435/252.31; 435/252.33; 435/254.11; 435/254.21; 435/254.22; 435/254.23; 435/254.3; 435/254.4; 435/254.5; 435/254.6; 435/320.1; 435/325; 536/23.2; 800/13; 800/298

(58) Field of Classification Search
None
See application file for complete search history.

(56) References Cited

U.S. PATENT DOCUMENTS

| | | | |
|---|---|---|---|
| 2004/0111763 A1* | 6/2004 | Heinz et al. .................. 800/281 |
| 2005/0273885 A1 | 12/2005 | Singh et al. | |
| 2007/0118929 A1 | 5/2007 | Damude et al. | |

FOREIGN PATENT DOCUMENTS

| | | |
|---|---|---|
| WO | WO 00/70945 A2 | 11/2000 |
| WO | WO 01/59128 A | 8/2001 |
| WO | WO 01/59128 A2 | 8/2001 |
| WO | WO 02/077213 A | 10/2002 |
| WO | 2005083093 A2 | 9/2005 |
| WO | WO 2006/008099 A | 1/2006 |
| WO | 2007061742 A1 | 5/2007 |

OTHER PUBLICATIONS

Whisstock et al. Quaterly Reviews of Biophysics, 2003, "Prediction of protein function from protein sequence and structure", 36(3): 307-340.*

Guo et al. Protein tolerance to random amino acid change, Proc Natl Aced Sci U S A. Jun. 22, 2004;10(25):9205-10. Epub Jun. 14, 2004.*

Expression of the Isochrysis C18-$\Delta^9$ Polyunsaturated Fatty Acid Specific Elongase Component Alters Arabidopsis Glycerolipid Profiles[1], Thomas Colin et al, Plant Physiology, Jun. 2004, vol. 135, pp. 859-866.

Production of Eicosapentaenoic and Docosahexaenoic Acid-Containing Oils in Transgenic Land Plants for Human and Aquaculture Nutrition, Stanley S. Robert, Marine Biotechnology, DOI: 10.1007, vol. 0, pp. 1-7 (2005).

Production of very long chain polyunsaturated omega-3 and omega-6 fatty acids in plants, Baoxiu Qi, et al, Nature Biotechnology, vol. 22, No. 6, Jun. 2004.

The alternative pathway $C_{20}\Delta 8$-desaturase from the non-photosynthetic organism *Acanthamoeba castellanii* is an atypical cytochrome $b_5$-fusion desaturase, Olga Sayanova et al, FEBS Letters 580, 2006, pp. 1946-1952.

Short Protocols in Molecular Biology, $2^{nd}$ edition, Harvard Medical School, Jun. 12, 2006.

Long-chain n-3 polyunsaturated fatty acid production by members of the marine protistan group the thraustochytrids: screening of isolates and optimisation of docosahexaenoic acid production, R,D. Bowles et al, Journal of Biotechnology, 70, 1999, pp. 193-202.

γ-Linolenic Acid: Recent Advances in Biotechnology and Clinical Applications, Tapas Das et al, AOCS Press, 2001, pp. 44-60.

(Continued)

*Primary Examiner* — Iqbal H Chowdhury
(74) *Attorney, Agent, or Firm* — Calfee, Halter & Griswold LLP

(57) ABSTRACT

The subject invention relates to the identification of a gene involved in the elongation of polyunsaturated fatty acids containing unsaturation at the carbon 9 position (i.e., "Δ9-elongase") and to uses thereof. In particular, Δ9-elongase may be utilized, for example, in the conversion of linoleic acid (LA, 18:2n-6) to eicosadienoic acid (EDA, 20:2n-6). The production of dihomo-γ-linolenic acid (DGLA, 20:3n-6) from eicosadienoic acid (EDA, 20:2n-6), and arachidonic acid (AA, 20:4n-6) from dihomo-γ-linolenic acid (DGLA, 20:3n-6) is then catalyzed by Δ8-desaturase and Δ5-desaturase, respectively. AA or polyunsaturated fatty acids produced therefrom may be added to pharmaceutical compositions, nutritional compositions, animal feeds, as well as other products such as cosmetics.

19 Claims, 15 Drawing Sheets

(56) References Cited

OTHER PUBLICATIONS

Lipids of Selected Molds Grown for Production of n-3 and n-6 Polyunsaturated Fatty Acids, Andrew Kendrick and Colin Ratledge, Lipids, vol. 27, No. 1, 1992, pp. 15-20. XP 002047887.

Arachidonic and docosahexaenoic acids are biosynthesized from their 18-carbon precursors in human infants, Norman Salem, Jr. et al, Biochemistry, vol. 93, pp. 49-54, Jan. 1996, XP-002131822.

Role of a New Mammalian Gene Family in the Biosynthesis of Very Long Chain Fatty Acids and Sphingolipids, Petr Tvrdik, et al., The Journal of Cell Biology, vol. 149, No. 3, May 1, 2000, pp. 707-717.

"The Variant 'His-Box' of the C18-Δ9-PUFA-Specific Elongase IgASE1 from *Isochlysis galbana* is Essential for Optimum Enzyme Activity," Baoxiu, Qi, et al, FEBS Letters 547, 2003, pp. 137-139.

"Identification of a cDNA Encoding a Novel C18-$\Delta^9$ Polyunsaturated Fatty Acid-Specific Elongating Activity from the Docosahexaenoic Acid (DHA)-Producing Microalga, *Isochrysis Galbana*[1]", Baoxiu Qi, et al, FEBS Letters 510, 2002, pp. 159-165.

Qi B et al: Identification of a cDNA . . . , FEBS Letters, vol. 510, No. 3, Jan. 16, 2002, pp. 159-165, XP004332633, ISSN: 0014-5793.

Qi B et al: Production of a very long chain pol . . . , Nature Biotechnology, Nature Publishing Group, vol. 22, No. 6, Jun. 1, 2004, p. 739-745, XP002348313, ISSN: 1087-0156.

Sayanova, et al., "Eicosapentaenoic Acid: Biosynthetic Routes and the Potential for Synthesis in Transgenic Plants," Phytochemistry, vol. 65(2), pp. 147-158 (2004).

Napier, et al., "The Production of Long Chain Polyunsaturated Fatty Acids in Transgenic Plants by Reverse Engineering," Biochemie, vol. 86(11), pp. 785-792 (2004).

Drexler, et al., "Metabolic Engineering of Fatty Acids for Breeding of New Oilseed Crops: Strategies, Problems and First Results," Journal of Plant Physiology, vol. 160(7), pp. 779-802 (2003).

International Preliminary Report on Patentability for PCT/US2007/084902, dated May 19, 2009.

\* cited by examiner

Figure 2

Full length Nucleotide Sequence of pRAT-5A1 pRAT-5A1 ORF Sequence: 819 bp (SEQ ID NO: 1)

atgggggacctcgaaagatacaagggcatggcggagtctttagccaagtacgccacgtcggcggccttcaagtggcaagtca
cgtacagcaaggaggacagctatgtaggcccgataatgatctccgaaccgctcgggctgctgggtagggtcaaccgcgctgtac
tttgtgacgctcgccgtcacgtacatgctgcgagggtatcttggcggacttatggcgctccgcggagcgcacaacctcggacttt
gtctgttttctggcgccgtatggatctatacgacctacctcatggtgcaggatgaccattttgcgagtctggaatcggcgacgtgca
aacggctcacgcacccgcatttttcagctcatcagtttcttgtttgcggcatccaaggtctgggagtggttcgacaccgtattgctcat
catcaagggcaacaagttgcgttttctgcatgtcttgcaccacgcaaccacctttggctttacgcaatcgaccacattttcctttcat
ccatcaagtatggtgtcgccgtgaatgcttttattcacacggtcatgtacgcgcactactttcgtcccttccccaagcagtttcgtcct
ctcattacgcagttgcagattgtgcagttcatctttagcattgctatccacacggcgatttactttcactatgactgcgagccgttggt
gcacacgcatttttacgagtacctgacgccatattacattgtggtcccccttcctctttctctttctcaacttttacgtgcagcagtacatt
ctcgcgccgtcaaagcccaagacaaaatctgcctaa

Figure 3

Full length Amino Acid Sequence of pRAT-5A1 pRAT-5A1 AA Sequence: 273 aa  (SEQ ID NO:2)

MGDLERYKGMAESLAKYATSAAFKWQVTYSKEDSYVGPIMISEPLGLLVGSTAL
YFVTLAVTYMLRGYLGGLMALRGAHNLGLCLFSGAVWIYTTYLMVQDDHFAS
LESATCKRLTHPHFQLISFLFAASKVWEWFDTVLLIIKGNKLRFLHVLHHATTFW
LYAIDHIFLSSIKYGVAVNAFIHTVMYAHYFRPFPKQFRPLITQLQIVQFIFSIAIHT
AIYFHYDCEPLVHTHFYEYLTPYYIVVPFLFLFLNFYVQQYILAPSKPKTKSA*

FIGURE 4

Amino Acid Sequence alignment of EST:660R1 (SEQ ID NO: 17) with TELO1 (SEQ ID NO: 18) and MELO4 (SEQ ID NO: 19)
>>ELO:TELO1                                                            (273 aa)
 initn: 146 init1:  79 opt: 295 Z-score: 70.9 expect(): 0.94
Smith-Waterman score: 295;    35.3% identity in 156 aa overlap
 (20-166:121-271)
                         10        20        30        40
660R1.pep              SGNSGRPCQNGSPHPHFQLISFLFAASKVWEWFDTVLLII--KGNKLRF
                         ::| :||::|::||:::|:   | |::  |
TELO1       TIRQAILGGYKVFGNDMEKGNESHAQGMSRIVYVFYVSKAYEFLDTAIMILCKKFNQVSF
                   100       110       120       130       140       150

50        60        70        80        90       100
660R1.pep  LHVLHHATTF--WLYAIDHIFLSSIKYGVAVNAFIHTVMYAHYFRP-----FPKQFRPLI
           ||| ||||  | |    : ::  ::| :|:|:|||||:||        | | ::| |
TELO1      LHVYHHATIFAIWWAIAKYAPGGDAYFSVILNSFVHTVMYAYYFFSSQGFGFVKPIKPYI
                   160       170       180       190       200       210

110       120       130       140       150       160
660R1.pep  TQLQIVQFIFSIAIHTAIYFHYDCEPLVHTHFYEYLTPYYIVVPFLFLFLNFYVQQYILA
           | ||::||:  :: :::    : : |:    : :      |   |::: :| ||  ||::||:|:
TELO1      TTLQMTQFM--AMLVQSLYDYLFPCD---YPQALVQLLGVYMIT-LLALFGNFFVQSYLKK
                   220       230       240       250       260

170       180       190       200       210       220
660R1.pep  PSKPKTKSAXDELSPTDSRLRFHXGTSLVXSQTFALHVCEDGTLVNECMNEYEFIFRCVF
           |:|  ||:
TELO1      PKKSKTN
                   270
>>ELO:MELO4                                                            (293 aa)
 initn: 128 init1:  52 opt: 246 Z-score: 58.5 expect(): 4.3
Smith-Waterman score: 246;    30.6% identity in 186 aa overlap
 (2-167:93-267)
                                                            10        20
660R1.pep                                       SGNSGRPCQN----GSPHPHFQLISFLFAAS
                                                |:  : |||    |   :   :::    |
MELO4       SLRGILTLYNLAITLLSAYMLVELILSSWEGGYNLQCQNLDSAGEGDVRVAKVLWWYYFS
                    70        80        90       100       110       120

30        40        50        60        70        80
660R1.pep  KVWEWFDTVLLII--KGNKLRFLHVLHHATTF--WLYAIDHIFLSSIKYGVAVNAFIHTV
           |: |:::||:::::     | |::  ||||  |||:  |   |   ::  :|  :| ::|:||| :
MELO4      KLVEFLDTIFFVLRKKTNQITFLHVYHHASMFNIWWCVLNWIPCGQSFFGPTLNSFIHIL
                   130       140       150       160       170       180

90       100       110       120       130
660R1.pep  MYAHY-FRPFPKQFRPL-----ITQLQIVQFIFSIAIHT--AIY----FHYDCEPLVHTH
           ||::| :  ||::  :  |      :|| |:|||:::|: ||   |:     |  :  |  |:
MELO4      MYSYYGLSVFPSMHKYLWWKKYLTQAQLVQFVLTIT-HTLSAVVKPCGFPFGC--LI---
                   190       200       210       220       230

140       150       160       170       180       190
660R1.pep  FYEYLTPYYIVVPFLFLFLNFYVQQYILAPSKPKTKSAXDELSPTDSRLRFHXGTSLVXS
             :  :|::::  ::||||||:|  |   | | : :
MELO4      ---FQSSYMMTL--VILFLNFYIQTYRKKPVKKELQEKEVKNGFPKAHLIVANGMTDKKA
                   240       250       260       270       280       290

200       210       220       230
660R1.pep  QTFALHVCEDGTLVNECMNEYEFIFRCVFXTHRLLPKKN
MELO4      Q pYX242 Vector Map and Restriction Sites:

Figure 6

Lipid Profile Data

|  | Fatty Acid Treatment | % Conversion | |
| --- | --- | --- | --- |
|  |  | Vector Alone pYX242 | pRAT-5A1 |
| LA (C18:2n-6) → EDA (C20:2n-6) | 50 uM | 0.9505 | 4.933 |
| ALA (C18:3n-3) → ETrA (C20:3n-3) | 50 uM | 2.1535 | 21.2175 |
| EPA (C20:5n-3) → DPA (C22:5n-3) | 50 uM | 0.2024 | 2.292 |

Figure 7

Amino acid sequence identity between elongase-encoded proteins from Danio rerio (SEQ ID NO:20) and pRAT-5A1 (SEQ ID 2). The consensus sequence (SEQ ID NO:21) is also shown.

```
                                                                              44
Danio rerio D9 elongase         (1)  ------------MSVLNLQEYEFERQFN------EDEAERWMQENWK
Translation of pRAT-5A1 ORF     (1)  MGDLERYKGMAESLAKYATSAAFKWQVTYSKEDSVGPDMISEP
Consensus                       (1)                      AL Y   F       ED  I  I 88
Danio rerio D9 elongase        (30)  KSFLFSELYAACHLGGRHVMKQREKFELRKPLVLWSLTLAAFSI
Translation of pRAT-5A1 ORF    (45)  LGLLVGSTALYFMTLAVTYMLRGYLGGLMALRGAHNLGLCLFSG
Consensus                      (45)  L  A   I A M      L       LL      FS 132
Danio rerio D9 elongase        (74)  FGAIRTGGYMVNILMTKGLKQSVCDQSFYNGPVSKFWAVAFVLS
Translation of pRAT-5A1 ORF    (89)  AVWIYTTYLMVQDDHFASLESGTCKR--LTHPHFQLISELRAAS
Consensus                      (89)       IT    MVN        L A C     P     AF F  S 176
Danio rerio D9 elongase       (118)  KAPELGDTEFEVERQKLIFLIWYHHITVLLYSWYSSKDMVAGG
Translation of pRAT-5A1 ORF   (131)  KVWEMFDIMLEIEKGNKLRFLHVLHHATTFWLYAIDHIFHSD-I
Consensus                     (133)  K  E    DTL IIIK NKL FLH HH  T       H  L A 220
Danio rerio D9 elongase       (162)  GNFMTMNVLNHAVMYESKYALRAAGFKISEKEAMFITLTQITQMV
Translation of pRAT-5A1 ORF   (174)  KMGIAVNAFHITVMYAHYFR-----PFPHQFRPLITQLQIVQFH
Consensus                     (177)  W M MN   IH VMYAHY            K F   IT QI Q I 264
Danio rerio D9 elongase       (206)  MGCVQNYLNYLWMQQGQECPSHVQNIFWSSLMYESVFVLTCQFH
Translation of pRAT-5A1 ORF   (213)  FSIAHHTAHYFHYDCEPLVHHFFYEYGTPYYHVMPHLFHLNFM
Consensus                     (221)      I    IY       SH       L   I ILF  LF NFF 281
Danio rerio D9 elongase       (250)  FEAYITKRKSNAAAKKSQ
Translation of pRAT-5A1 ORF   (257)  VQQYLLAPSKPFKTKSA-
Consensus                     (265)          YI    K A
```

Figure 8

Amino acid sequence identity between Δ9 elongase-encoded proteins from Isochrysis galbana (SEQ ID NO:22) and pRAT-5A1 (SEQ ID 2). The consensus sequence (SEQ ID NO:23) is also shown.

```
                                                                                          1                                                          44
I galbana D9 elongase         (1)   ------MVIIANDACERIWNAVTDPEWLIGTFSYLILKPFIHRN-
Translation of pRAT-5A1 ORF   (1)   MGDLERYKCMAESLIKYATSAAFKWQVTYSKEDSYAGPIWESEP
Consensus                     (1)                ALA  A    AA    I       L    LI
                                     45                                                                88
I galbana D9 elongase        (37)   SGLNDEKKGAYRTSMIWYNLLALFSAIGSFVVTATALGWDYGIG
Translation of pRAT-5A1 ORF  (45)   LGLIVGSTALYFVILAVTVMLRSYLGGMALRGAHNLGLCLFIG
Consensus                    (45)   GLL    A Y  SL    ML A   AL   A   LG      SG
                                     89                                                               132
I galbana D9 elongase        (81)   AWLRRQT-----GDTPQPLFQCPSPVMDSKLFTWTAKAFYYSKY
Translation of pRAT-5A1 ORF  (89)   AVWIYTTYLMVQDDHFASLESATCKRLTHPFQLISFLFAASKV
Consensus                    (89)   A       T   D  L              F    A  F   SK
                                    133                                                               176
I galbana D9 elongase       (120)   VEXLDTAWLNIKGKRNSFLQAPHHFGAPWDMYLGIRHHNEGWMI
Translation of pRAT-5A1 ORF (133)   WFWFDTVLIEIKGNQERFLHVLMHATTFW-HVAIDHFLSSIKY
Consensus                   (133)   EW DT  L  IKG KL FL   HH     W LY   I      I
                                    177                                                               220
I galbana D9 elongase       (164)   FIFFNSEIHTMTNYGLTAAGKKFKASPLTANQICQFNG-GF
Translation of pRAT-5A1 ORF (176)   GVAVNEFHHIMYAHY---FRPEPKQFHPFTQHQIVQFFPSIA
Consensus                   (177)   M NAFIHTIMY HY       F     KPLIT LQI QFI
                                    221                                                               264
I galbana D9 elongase       (207)   ILVWDYINVPCFNSDKGKLEWAFNYAVVGSVFLFCHFIYQDN
Translation of pRAT-5A1 ORF (217)   IHTAIYFHYDCEPLVHTHFIEITPYYIVPPLFLIFLNFWVQQY
Consensus                   (221)   I    Y    C         F W   Y V    LF   FF Q
                                    265                                                               277
I galbana D9 elongase       (251)   IATKKSAKAGKQL
Translation of pRAT-5A1 ORF (261)   ILAPSKPKTKSA-
Consensus                   (265)   I      K
```

Figure 9

Amino acid sequence identity between Δ9 elongase-encoded proteins from Pavlova salina (SEQ ID NO:24) and pRAT-5A1 (SEQ ID 2). The consensus sequence (SEQ ID NO:25) is also shown.

```
                                                                                        38
Pav salina D9 elo (direct 1)   (1)  MGPLSTLLAMMPEWGERVAGLTLVERQQMSEELVRANK
Translation of pRAT-5A1 ORF    (1)  MGDLERYKQTAESLAKLATSAAFKWQVTYSKEDSYVGP
                 Consensus     (1)  MG L    A    S A  F           S  E
                                    39                                                  76
Pav salina D9 elo (direct 1)  (39)  IPTSLIPEVDFVTIASVYVGDHWRIPFTAISAYLVLHT
Translation of pRAT-5A1 ORF   (39)  LMLSEP------------------NGLLVGSTALYFMT
                 Consensus    (39)  I IS                        I    S  L IT
                                    77                                                 114
Pav salina D9 elo (direct 1)  (77)  LEPQLMARRPPLPENTLACLWNFELSLEFSVGMIVTWT
Translation of pRAT-5A1 ORF   (59)  LAVTYMLRGYLGGHMALRGAHNLGCLFSGAVMIVTTY
                 Consensus    (77)  L   M R      I L  N AL LFS        I T
                                    115                                                152
Pav salina D9 elo (direct 1) (115)  TWGERIMWKNGHEDTVCGHPIFMGGWIGYMLAFIWSK
Translation of pRAT-5A1 ORF   (97)  LMVQDDHFASHESATCKR---TIPHFQLHSFLPAASK
                 Consensus   (115)      I       IE  C       L H        F   SK
                                    153                                                190
Pav salina D9 elo (direct 1) (153)  HELIDTVFLIAKKADVIELHWYIHNVIVLLHCWHSYAN
Translation of pRAT-5A1 ORF  (132)  LMEWPTVLLHIIKGNKHRFIHVLHHATT-FMLMAIDHH
                 Consensus   (153)  LFE  DTV LI K   L FLH    HH T  W W    I
                                    191                                                228
Pav salina D9 elo (direct 1) (191)  RHPSGINFAAMNYFMHAHMYAHEGMTQIGFPRQKLVRP
Translation of pRAT-5A1 ORF  (169)  FHSSIKGVAVMAFHHTVMYAHH------FRPFPNQ
                 Consensus   (191)  I S W  AMN FIH IMYAHF              R    K
                                    229                                                266
Pav salina D9 elo (direct 1) (229)  MARLHTFQHSQMGVGHAVNGLIIRHPSIGHHCHSNKT
Translation of pRAT-5A1 ORF  (199)  HRPLTFQLQHVQFIFSHAHHTAIYFHYDCEPLVHHHFY
                 Consensus   (229)  F  LIT QI Q     IAI    I  H        HS
                                    267                                                304
Pav salina D9 elo (direct 1) (267)  NTHLSHLNVASHFVLFAALVVKNVIFSKLKSPKRKKVE
Translation of pRAT-5A1 ORF  (237)  EYHTPMYPVVPHLFLFLNFYVQQVILPSK-PKTKSA-
                 Consensus   (267)    I    W I   F    F  LF   YV NYI A  K PK K
                                    305
Pav salina D9 elo (direct 1) (305)  -
Translation of pRAT-5A1 ORF  (273)  -
                 Consensus   (305)
```

Figure 10

Amino acid sequence identity between proteins encoded by Thraustochytrium sp. FJN-10 (SEQ ID NO:26) and pRAT-5A1 (SEQ ID 2). The consensus sequence (SEQ ID NO:27) is also shown.

```
                                                                             44
T.Aureum FJN 10 D9 elongase     (1) MMEPLDRYEDIAELAAEVASSAATKWQVTYDAKDSEVGPEGIRE
Translation of pRAT-5A1 ORF     (1) -MGDLDRYKGMAESLAKVAMSAAFKWQVTYSKEDSEVGPEMISE
                  Consensus     (1)   M  LDRYKALAE AKYASSAAFKWQVTY   DSFVGPI I E 88
T.Aureum FJN 10 D9 elongase    (45) PLGLIVGSVVLYLSLQAVVYALRNYLGGLMALRSVHNLGLCLFS
Translation of pRAT-5A1 ORF    (44) PLGLIVGSTALYFVTLAVTYMLRGYLGGLMALRGAHNLGLCLFS
                  Consensus    (45) PLGLIVGS  LY   AV Y LR YLGGLMALR  HNLGLCLFS 132
T.Aureum FJN 10 D9 elongase    (89) GAVWMIYTSYLMMQDGHPRSLEAATCEPLKHPHPQLISLLFALSK
Translation of pRAT-5A1 ORF    (88) GAVWIYTEYLMVQDDHPASLESATCKRLTHPHFQLISFLFAASK
                  Consensus    (89) GAVWIYTSYLMIQD HF SLEAATC  L  HPHFQLIS LFA SK 176
T.Aureum FJN 10 D9 elongase   (133) IWEWFDTVLLIIVKGNKLRFLHVLHHATTFWLYAIDHIFLSSIKY
Translation of pRAT-5A1 ORF   (132) VWEWFDTVLLIEIKGNKLRFLHVLHHATTFWLYAIDHIFLSSIKY
                  Consensus   (133) IWEWFDTVLLIIKGNKLRFLHVLHHATTFWLYAIDHIFLSSIKY 220
T.Aureum FJN 10 D9 elongase   (177) GVAVNAFIHTVMYAHYFRPFPKGLRPLITQLQIVQFIFSTCIHT
Translation of pRAT-5A1 ORF   (176) GVAVNAFIHTVMYAHYFRPFPKQFRPLITQLQIVQFIFSTAIHT
                  Consensus   (177) GVAVNAFIHTVMYAHYFRPFPK   RPLITQLQIVQFIFSIAIHT 264
T.Aureum FJN 10 D9 elongase   (221) AIYMHYDCEPLVHTHFWEYLTPYLFVVPFLIFLNFVQQYMLA
Translation of pRAT-5A1 ORF   (220) AIYFHYDCEPLVHTHFWEYLTPYIVFLFLNFYQQYLA
                  Consensus   (221) AIYFHYDCEPLVHTHFWEVLTPY  VVPFL LFLNFYLQQYILA T.Aureum FJN 10 D9 elongase   (265) PEKTKKA---
Translation of pRAT-5A1 ORF   (264) PEKPKTKSA-
                  Consensus   (265) PAK K
```

Figure 11

Amino acid sequence alignment of proteins encoded by pRAT-5A1 (SEQ ID NO:2), pRAT-5A1 mutant 1 (SEQ ID NO:5) and pRAT-5A1 mutant 2 (SEQ ID NO:6)

Conserved amino acid sequence motifs present in other PUFA-elongases are underlined in pRAT-5A1 sequence. These include the 'Histidine-box motif' and the 'HXYMY' motif. Amino acid residue changes created in the mutant sequences by site-directed mutagenesis are underlined & highlighted.

```
                          1                                                                70
pRAT-5A1          (1)    MGDLERYKGMAESLAKYATSAAFKWQVTYSKEDSYVGPIMISEPLGLLVGSTALYFVTLAVTYMLRGYLG
pRAT-5-A1 mutant 1 (1)    MGDLERYKGMAESLAKYATSAAFKWQVTYSKEDSYVGPIMISEPLGLLVGSTALYFVTLAVTYMLRGYLG
pRAT-5-A1 mutant 2 (1)    MGDLERYKGMAESLAKYATSAAFKWQVTYSKEDSYVGPIMISEPLGLLVGSTALYFVTLAVTYMLRGYLG 71                                                               140
pRAT-5A1          (71)   GLMALRGAHNLGLCLFSGAVWIYTTYLMVQDDHFASLESATCKRLTHPFQLISFLFAASKVWEWFDTVL
pRAT-5-A1 mutant 1 (71)   GLMALRGAHNLGLCLFSGAVWIYTTYLMVQDDHFASLESATCKRLTHPFQLISFLFAASKVWEWFDTVL
pRAT-5-A1 mutant 2 (71)   GLMALRGAHNLGLCLFSGAVWIYTTYLMVQDDHFASLESATCKRLTHPFQLISFLFAASKVWEWFDTVL 141                                                              210
pRAT-5A1          (141)  LIIKGNKLRFLHVLHHATTFWLYAIDHIFLSSIKYGVAVNAFIHTVMYAHYFRPFPKQFRPLITQLQIVQ
pRAT-5-A1 mutant 1 (141)  LIIKGNKLRFLHVLRAPHVLDDATTFWLYAIDHIFLSSIKYGVAVNAFIHTVMYAHYFRPFPKQFRPLITQLQIVQ
pRAT-5-A1 mutant 2 (141)  LIIKGNKLRFLHVLHHATTFWLYAIDHIFLSSIKYGVAVNAFIDTVAAAHYFRPFPKQFRPLITQLQIVQ 211                                                              273
pRAT-5A1          (211)  FIFSIAIHTAIYFHYDCEPLVHTHFYEYLTPYYIVPFLFLFLNFYVQQYILAPSKPKTKSA-
pRAT-5-A1 mutant 1 (211)  FIFSIAIHTAIYFHYDCEPLVHTHFYEYLTPYYIVPFLFLFLNFYVQQYILAPSKPKTKSA-
pRAT-5-A1 mutant 2 (211)  FIFSIAIHTAIYFHYDCEPLVHTHFYEYLTPYYIVPFLFLFLNFYVQQYILAPSKPKTKSA-
```

Figure 12:
Expression studies with pRAT-5A1 mutants

| Plasmids in yeast | 18:2 n-6 Incorporated | 20:2 n-6 Produced | % Conversion* | % Decrease in Activity* | 18:3 n-3 Incorporated | 20:3 n-3 Produced | % Conversion* | % Decrease in Activity* |
|---|---|---|---|---|---|---|---|---|
| PYX242 (control) | 54.95 | 2.63 | 4.56 | N/A | 73.24 | 4.62 | 5.95 | N/A |
| PRAT-5A1 | 51.00 | 10.78 | 17.44 | N/A | 52.46 | 22.04 | 29.59 | N/A |
| PRAT-5A1 Mutant 1 | 45.06 | 4.21 | 8.55 | 50 | 37.68 | 4.21 | 10.12 | 65 |
| PRAT-5A1 Mutant 2 | 47.76 | 3.28 | 6.44 | 63 | 52.08 | 4.18 | 7.46 | 74.66 |

50 μM substrate added
Key:
18:2n-6 = Linoleic acid
20:2 n-6 = ω6-eicosadienoic acid
18:3 n-3 = γ-Linolenic acid
20:2 n-3 = ω3-eicosatrienoic acid

* % Conversion = [% Product]/ [% substrate + % Product] x 100
* Percent decrease in activity as compared to pRAT-5A1

Figure 13

Amino acid sequence alignment of proteins encoded by pRAT-5A1, pRAT-5A11 and pRAT-5B6

Differences in the amino acid residues present in pRAT-5A11- and pRAT-5B6-encoded proteins (SEQ ID NO:15 & SEQ ID NO:16) as compared to pRAT-5A1-encoded protein (SEQ ID NO:2) are underlined and highlighted.

```
                    1                                                                         70
pRAT-5A1     (1)    MGDLERYKGMAESLAKYATSAAFKWQVTYSKEDSYVGPIMISEPLGLLVGSTALYFVTLAVTYMLRGYLG
pRAT-5A11    (1)    MGDLERYKGMAESLAKYATSAAFKWQVTYSKEDSYVGPIMISEPLGLLVGSTALYFVTLAVTYMLRGYLG
pRAT-5B6     (1)    MGDLERYKGMAESLAKYATSAAFKWQVTYSKEDSYVGPMMISEPLGLLIGSTALYFVTLAVTYMLRGYLG 71                                                                        140
pRAT-5A1     (71)   GLMALRGAHNLGLCLFSGAVWIYTTYLMVQDDHFASLESATCKRLTHPHFQLISFLFAASKVWEWFDTVL
pRAT-5A11    (71)   GPMALRGAHNLGLCLFSGAVWIYTTYLMVQDDHFASLESATCKRLTHLHFQLISFLFAASKVWEWFDTVL
pRAT-5B6     (71)   GLMALRGAHNLGLCLFSGAVWIYTTYLMVQNDHFASLESATCKRLTHPHFQLISFLFAASKVWEWFDTVL 141                                                                       210
pRAT-5A1     (141)  LIIKGNKLRFLHVLHHATTFWLYAIDHIFLSSIKYGVAVNAFIHTVMYAHYFRPFPKQFRPLITQLQIVQ
pRAT-5A11    (141)  LIIKGNKLRFLHVLHHATTFWLYAIDHIFLSSIKYGVAVNAFIHTVMYAHYFRPFPKQFRPLITQLQIVQ
pRAT-5B6     (141)  LIIKGNKLRFLHVLHHATTFWLYAIDHIFLSSIKYGVAVNAFIHTVMYAHYFRPFPKQFRPLITQLQIVQ 211                                          273
pRAT-5A1     (211)  FIFSIAIHTAIYFHYDCEPLVHTHFYEYLTPYYIVVPFLFLFLNFYVQQYILAPSKPKTKSA-
pRAT-5A11    (211)  FIFSIAIHTAIYFHYDCEPLVHTHFYEYLTPYYIVVPFLFLFLNFYVQQYILAPSKPKTKSA-
pRAT-5B6     (211)  FIFSIAIHTAIYFHYDCEPLVHTHFYEYLTPYYIVVPFLFLFLNFYVQQYILAPSKPKTKSA-
``` pRS1 vector map

Figure 15:

Fatty acid profile of transgenic seeds expressing pRAT-5A1 versus non-transgenic seeds (wild-type)

20:2 n-6 (bold) appears to be the major product generated due to elongation of 18:2 n-6 (bold) by the pRAT-5A1-encoded elongase in the transgenic seed lines. No 20:2 n-6 product is detected in wild-type lines.

|  | pRAT-5A1 transgenic seeds | | | | |
|---|---|---|---|---|---|
| Fatty acids (% Total Fatty acids) | Line 1 | Line 2 | Line 3 | Line 4 | Line 5 |
| 16:0 | 5.8 | 6.6 | 2.8 | 4.7 | 7.2 |
| 18:0 | 10.5 | 9.4 | 12.4 | 10.6 | 9.5 |
| 18:1 n-9 | 18.7 | 24.3 | 14.6 | 24.4 | 24.0 |
| 18:2 n-6 | 49.2 | 44.0 | 37.6 | 41.9 | 42.3 |
| 18:3 n-3 | 1.3 | 1.3 | 2.2 | 1.1 | 1.1 |
| 20:0 | 1.1 | 1.4 | 2.8 | 1.4 | 1.7 |
| 20:1 n-9 | 3.6 | 5.2 | 7.5 | 4.0 | 4.5 |
| 20:2 n-6 | 7.2 | 6.4 | 13.5 | 8.4 | 7.1 |
| 22:2 n-6 | 1.7 | 1.4 | 4.3 | 2.2 | 1.9 |
| other C20 & C22 | 0.8 | 0.0 | 2.3 | 1.1 | 0.9 |
| total C20 + C22 | 14.5 | 14.4 | 30.4 | 17.2 | 16.0 |

|  | wild type-fad3/fae1 seeds (control) | | | | |
|---|---|---|---|---|---|
| Fatty acids (% Total Fatty acids) | Seed 1 | Seed 2 | Seed 3 | Seed 4 | Seed 5 |
| 16:0 | 8.7 | 8.4 | 6.9 | 8.9 | 8.0 |
| 18:0 | 4.9 | 3.9 | 3.2 | 5.3 | 3.8 |
| 18:1 n-9 | 30.8 | 34.7 | 40.6 | 32.5 | 31.1 |
| 18:2 n-6 | 51.9 | 49.6 | 46.8 | 50.9 | 53.6 |
| 18:3 n-3 | 1.9 | 1.8 | 1.0 | 1.3 | 1.5 |
| 20:0 | 0.9 | 0.7 | 0.8 | 1.0 | 0.8 |
| 20:1 n-9 | 0.3 | 0.4 | 0.4 | 0.2 | 0.5 |
| 20:2 n-6 | 0.0 | 0.0 | 0.0 | 0.0 | 0.0 |
| 22:2 n-6 | 0.3 | 0.2 | 0.0 | 0.0 | 0.5 |
| other C20 & C22 | 0.2 | 0.2 | 0.2 | 0.0 | 0.3 |
| total C20 + C22 | 1.8 | 1.6 | 1.4 | 1.2 | 2.1 |

SEQUENCE LISTING

<160> NUMBER OF SEQ ID NOS: 27

<210> SEQ ID NO 1
<211> LENGTH: 819
<212> TYPE: DNA
<213> ORGANISM: Thraustochytrid sp. BICC 7087

<400> SEQUENCE: 1

```
atgggggacc tcgaaagata caagggcatg gcggagtctt tagccaagta cgccacgtcg      60
gcggccttca gtggcaagt cacgtacagc aaggaggaca gctatgtagg cccgataatg     120
atctccgaac cgctcgggct gctggtaggg tcaaccgcgc tgtactttgt gacgctcgcc     180
gtcacgtaca tgctgcgagg gtatcttggc ggacttatgg cgctccgcgg agcgcacaac     240
ctcggacttt gtctgttttc tggcgccgta tggatctata cgacctacct catggtgcag     300
gatgaccatt ttgcgagtct ggaatcggcg acgtgcaaac ggctcacgca cccgcatttt     360
cagctcatca gtttcttgtt tgcggcatcc aaggtctggg agtggttcga caccgtattg     420
ctcatcatca agggcaacaa gttgcgtttt ctgcatgtct tgcaccacgc aaccaccttt     480
tggctttacg caatcgacca cattttcctt tcatccatca gtatggtgt cgccgtgaat     540
gcttttattc acacggtcat gtacgcgcac tactttcgtc ccttccccaa gcagtttcgt     600
cctctcatta cgcagttgca gattgtgcag ttcatcttta gcattgctat ccacacggcg     660
atttactttc actatgactg cgagccgttg gtgcacacgc attttacga gtacctgacg      720
ccatattaca ttgtggtccc cttcctcttt ctctttctca acttttacgt gcagcagtac     780
attctcgcgc cgtcaaagcc aagacaaaa tctgcctaa                             819
```

<210> SEQ ID NO 2
<211> LENGTH: 272
<212> TYPE: PRT
<213> ORGANISM: Thraustochytrid sp. BICC 7087

<400> SEQUENCE: 2

```
Met Gly Asp Leu Glu Arg Tyr Lys Gly Met Ala Glu Ser Leu Ala Lys
1               5                  10                  15

Tyr Ala Thr Ser Ala Ala Phe Lys Trp Gln Val Thr Tyr Ser Lys Glu
            20                  25                  30

Asp Ser Tyr Val Gly Pro Ile Met Ile Ser Glu Pro Leu Gly Leu Leu
        35                  40                  45

Val Gly Ser Thr Ala Leu Tyr Phe Val Thr Leu Ala Val Thr Tyr Met
    50                  55                  60

Leu Arg Gly Tyr Leu Gly Gly Leu Met Ala Leu Arg Gly Ala His Asn
65                  70                  75                  80

Leu Gly Leu Cys Leu Phe Ser Gly Ala Val Trp Ile Tyr Thr Thr Tyr
                85                  90                  95

Leu Met Val Gln Asp Asp His Phe Ala Ser Leu Glu Ser Ala Thr Cys
            100                 105                 110

Lys Arg Leu Thr His Pro His Phe Gln Leu Ile Ser Phe Leu Phe Ala
        115                 120                 125

Ala Ser Lys Val Trp Glu Trp Phe Asp Thr Val Leu Leu Ile Ile Lys
    130                 135                 140

Gly Asn Lys Leu Arg Phe Leu His Val Leu His His Ala Thr Thr Phe
145                 150                 155                 160

Trp Leu Tyr Ala Ile Asp His Ile Phe Leu Ser Ser Ile Lys Tyr Gly
                165                 170                 175
```

```
Val Ala Val Asn Ala Phe Ile His Thr Val Met Tyr Ala His Tyr Phe
            180                 185                 190

Arg Pro Phe Pro Lys Gln Phe Arg Pro Leu Ile Thr Gln Leu Gln Ile
            195                 200                 205

Val Gln Phe Ile Phe Ser Ile Ala Ile His Thr Ala Ile Tyr Phe His
            210                 215                 220

Tyr Asp Cys Glu Pro Leu Val His Thr His Phe Tyr Glu Tyr Leu Thr
225                 230                 235                 240

Pro Tyr Tyr Ile Val Val Pro Phe Leu Phe Leu Phe Leu Asn Phe Tyr
                245                 250                 255

Val Gln Gln Tyr Ile Leu Ala Pro Ser Lys Pro Lys Thr Lys Ser Ala
            260                 265                 270

<210> SEQ ID NO 3
<211> LENGTH: 29
<212> TYPE: DNA
<213> ORGANISM: Thraustochytrid sp. BICC 7087

<400> SEQUENCE: 3
agaagaccat gggggacctc gaaagatac                                       29

<210> SEQ ID NO 4
<211> LENGTH: 32
<212> TYPE: DNA
<213> ORGANISM: Thraustochytrid sp. BICC 7087

<400> SEQUENCE: 4
agagctaagc ttaggcagat tttgtcttgg gc                                   32

<210> SEQ ID NO 5
<211> LENGTH: 272
<212> TYPE: PRT
<213> ORGANISM: Thraustochytrid sp. BICC 7087

<400> SEQUENCE: 5

Met Gly Asp Leu Glu Arg Tyr Lys Gly Met Ala Glu Ser Leu Ala Lys
1               5                   10                  15

Tyr Ala Thr Ser Ala Ala Phe Lys Trp Gln Val Thr Tyr Ser Lys Glu
            20                  25                  30

Asp Ser Tyr Val Gly Pro Ile Met Ile Ser Glu Pro Leu Gly Leu Leu
            35                  40                  45

Val Gly Ser Thr Ala Leu Tyr Phe Val Thr Leu Ala Val Thr Tyr Met
        50                  55                  60

Leu Arg Gly Tyr Leu Gly Gly Leu Met Ala Leu Arg Gly Ala His Asn
65                  70                  75                  80

Leu Gly Leu Cys Leu Phe Ser Gly Ala Val Trp Ile Tyr Thr Thr Tyr
                85                  90                  95

Leu Met Val Gln Asp Asp His Phe Ala Ser Leu Glu Ser Ala Thr Cys
            100                 105                 110

Lys Arg Leu Thr His Pro His Phe Gln Leu Ile Ser Phe Leu Phe Ala
            115                 120                 125

Ala Ser Lys Val Trp Glu Trp Phe Asp Thr Val Leu Leu Ile Ile Lys
        130                 135                 140

Gly Asn Lys Leu Arg Ala Pro His Val Leu Asp Asp Ala Thr Thr Phe
145                 150                 155                 160

Trp Leu Tyr Ala Ile Asp His Ile Phe Leu Ser Ser Ile Lys Tyr Gly
                165                 170                 175
```

```
Val Ala Val Asn Ala Phe Ile His Thr Val Met Tyr Ala His Tyr Phe
            180                 185                 190

Arg Pro Phe Pro Lys Gln Phe Arg Pro Leu Ile Thr Gln Leu Gln Ile
            195                 200                 205

Val Gln Phe Ile Phe Ser Ile Ala Ile His Thr Ala Ile Tyr Phe His
            210                 215                 220

Tyr Asp Cys Glu Pro Leu Val His Thr His Phe Tyr Glu Tyr Leu Thr
225                 230                 235                 240

Pro Tyr Tyr Ile Val Val Pro Phe Leu Phe Leu Phe Leu Asn Phe Tyr
                245                 250                 255

Val Gln Gln Tyr Ile Leu Ala Pro Ser Lys Pro Lys Thr Lys Ser Ala
            260                 265                 270
```

<210> SEQ ID NO 6
<211> LENGTH: 271
<212> TYPE: PRT
<213> ORGANISM: Thraustochytrid sp. BICC 7087

<400> SEQUENCE: 6

```
Met Gly Asp Leu Glu Arg Tyr Lys Gly Met Ala Glu Ser Leu Ala Lys
1               5                   10                  15

Tyr Ala Thr Ser Ala Ala Phe Lys Trp Gln Val Thr Tyr Ser Lys Glu
            20                  25                  30

Asp Ser Tyr Val Gly Pro Ile Met Ile Ser Glu Pro Leu Gly Leu Leu
            35                  40                  45

Val Gly Ser Thr Ala Leu Tyr Phe Val Thr Leu Ala Val Thr Tyr Met
            50                  55                  60

Leu Arg Gly Tyr Leu Gly Gly Leu Met Ala Leu Arg Gly Ala His Asn
65              70                  75                  80

Leu Gly Leu Cys Leu Phe Ser Gly Ala Val Trp Ile Tyr Thr Thr Tyr
                85                  90                  95

Leu Met Val Gln Asp Asp His Phe Ala Ser Leu Glu Ser Ala Thr Cys
            100                 105                 110

Lys Arg Leu Thr His Pro His Phe Gln Leu Ile Ser Phe Leu Phe Ala
            115                 120                 125

Ala Ser Lys Val Trp Glu Trp Phe Asp Thr Val Leu Leu Ile Ile Lys
            130                 135                 140

Gly Asn Lys Leu Arg Phe Leu His Val Leu His His Ala Thr Thr Phe
145                 150                 155                 160

Trp Leu Tyr Ala Ile Asp His Ile Phe Leu Ser Ser Ile Lys Tyr Gly
                165                 170                 175

Val Ala Val Asn Ala Phe Ile Asp Thr Val Ala Ala Ala His Tyr Phe
            180                 185                 190

Arg Pro Phe Pro Lys Gln Phe Arg Pro Leu Ile Thr Gln Leu Gln Ile
            195                 200                 205

Val Gln Ile Phe Ser Ile Ala Ile His Thr Ala Ile Tyr Phe His Tyr
            210                 215                 220

Asp Cys Glu Pro Leu Val His Thr His Phe Tyr Glu Tyr Leu Thr Pro
225                 230                 235                 240

Tyr Tyr Ile Val Val Pro Phe Leu Phe Leu Phe Leu Asn Phe Tyr Val
                245                 250                 255

Gln Gln Tyr Ile Leu Ala Pro Ser Lys Pro Lys Thr Lys Ser Ala
            260                 265                 270
```

<210> SEQ ID NO 7

-continued

```
<211> LENGTH: 20
<212> TYPE: DNA
<213> ORGANISM: Thraustochytrid sp. BICC 7087

<400> SEQUENCE: 7
agtgaacttg caacatttac                                               20

<210> SEQ ID NO 8
<211> LENGTH: 58
<212> TYPE: DNA
<213> ORGANISM: Thraustochytrid sp. BICC 7087

<400> SEQUENCE: 8
aagccaaaag gtggttgcgt cgtccaagac atgcggcgca cgcaacttgt tgcccttg     58

<210> SEQ ID NO 9
<211> LENGTH: 18
<212> TYPE: DNA
<213> ORGANISM: Thraustochytrid sp. BICC 7087

<400> SEQUENCE: 9
cgacggccag tgaattgt                                                 18

<210> SEQ ID NO 10
<211> LENGTH: 58
<212> TYPE: DNA
<213> ORGANISM: Thraustochytrid sp. BICC 7087

<400> SEQUENCE: 10
caagggcaac aagttgcgtg cgccgcatgt cttggacgac gcaaccacct tttggctt     58

<210> SEQ ID NO 11
<211> LENGTH: 53
<212> TYPE: DNA
<213> ORGANISM: Thraustochytrid sp. BICC 7087

<400> SEQUENCE: 11
agggacgaaa gtagtgcgcc gccgcgaccg tgtcaataaa agcattcacg gcg          53

<210> SEQ ID NO 12
<211> LENGTH: 53
<212> TYPE: DNA
<213> ORGANISM: Thraustochytrid sp. BICC 7087

<400> SEQUENCE: 12
cgccgtgaat gcttttattg acacggtcgc ggcggcgcac tactttcgtc cct          53

<210> SEQ ID NO 13
<211> LENGTH: 33
<212> TYPE: DNA
<213> ORGANISM: Thraustochytrid sp. BICC 7087

<400> SEQUENCE: 13
tatgaattca aaatggggga cctcgaaaga tac                                33

<210> SEQ ID NO 14
<211> LENGTH: 32
<212> TYPE: DNA
<213> ORGANISM: Thraustochytrid sp. BICC 7087

<400> SEQUENCE: 14
tatactcgag ttaggcagat tttgtcttgg gc                                 32
```

<210> SEQ ID NO 15
<211> LENGTH: 272
<212> TYPE: PRT
<213> ORGANISM: Thraustochytrid sp. BICC 7087

<400> SEQUENCE: 15

```
Met Gly Asp Leu Glu Arg Tyr Lys Gly Met Ala Glu Ser Leu Ala Lys
1               5                   10                  15

Tyr Ala Thr Ser Ala Ala Phe Lys Trp Gln Val Thr Tyr Ser Lys Glu
            20                  25                  30

Asp Ser Tyr Val Gly Pro Met Met Ile Ser Glu Pro Leu Gly Leu Leu
        35                  40                  45

Ile Gly Ser Thr Ala Leu Tyr Phe Val Thr Leu Ala Val Thr Tyr Met
50                  55                  60

Leu Arg Gly Tyr Leu Gly Gly Pro Met Ala Leu Arg Gly Ala His Asn
65                  70                  75                  80

Leu Gly Leu Cys Leu Phe Ser Gly Ala Val Trp Ile Tyr Thr Thr Tyr
                85                  90                  95

Leu Met Val Gln Asp Asp His Phe Ala Ser Leu Glu Ser Ala Thr Cys
            100                 105                 110

Lys Arg Leu Thr His Leu His Phe Gln Leu Ile Ser Phe Leu Phe Ala
        115                 120                 125

Ala Ser Lys Val Trp Glu Trp Phe Asp Thr Val Leu Leu Ile Ile Lys
130                 135                 140

Gly Asn Lys Leu Arg Phe Leu His Val Leu His His Ala Thr Thr Phe
145                 150                 155                 160

Trp Leu Tyr Ala Ile Asp His Ile Phe Leu Ser Ser Ile Lys Tyr Gly
                165                 170                 175

Val Ala Val Asn Ala Phe Ile His Thr Val Met Tyr Ala His Tyr Phe
            180                 185                 190

Arg Pro Phe Pro Lys Gln Phe Arg Pro Leu Ile Thr Gln Leu Gln Ile
        195                 200                 205

Val Gln Phe Ile Phe Ser Ile Ala Ile His Thr Ala Ile Tyr Phe His
210                 215                 220

Tyr Asp Cys Glu Pro Leu Val His Thr His Phe Tyr Gly Tyr Leu Thr
225                 230                 235                 240

Pro Tyr Tyr Ile Val Val Pro Phe Leu Phe Leu Phe Leu Asn Phe Tyr
                245                 250                 255

Val Gln Gln Tyr Ile Leu Ala Pro Ser Lys Pro Lys Thr Lys Ser Ala
            260                 265                 270
```

<210> SEQ ID NO 16
<211> LENGTH: 272
<212> TYPE: PRT
<213> ORGANISM: Thraustochytrid sp. BICC 7087

<400> SEQUENCE: 16

```
Met Gly Asp Leu Glu Arg Tyr Lys Gly Met Ala Glu Ser Leu Ala Lys
1               5                   10                  15

Tyr Ala Thr Ser Ala Ala Phe Lys Trp Gln Val Thr Tyr Ser Lys Glu
            20                  25                  30

Asp Ser Tyr Val Gly Pro Ile Met Ile Ser Glu Pro Leu Gly Leu Leu
        35                  40                  45

Val Gly Ser Thr Ala Leu Tyr Phe Val Thr Leu Ala Val Thr Tyr Met
50                  55                  60

Leu Arg Gly Tyr Leu Gly Gly Leu Met Ala Leu Arg Gly Ala His Asn
```

```
                65                  70                  75                  80
Leu Gly Leu Cys Leu Phe Ser Gly Ala Val Trp Ile Tyr Thr Thr Tyr
                    85                  90                  95

Leu Met Val Gln Asn Asp His Phe Ala Ser Leu Glu Ser Ala Thr Cys
                    100                 105                 110

Lys Arg Leu Thr His Pro His Phe Gln Leu Ile Ser Phe Leu Phe Ala
                    115                 120                 125

Ala Ser Lys Val Trp Glu Trp Phe Asp Thr Val Leu Leu Ile Ile Lys
                130                 135                 140

Gly Asn Lys Leu Arg Phe Leu His Val Leu His His Ala Thr Thr Phe
145                 150                 155                 160

Trp Leu Tyr Ala Ile Asp His Ile Phe Leu Ser Ser Ile Lys Tyr Gly
                    165                 170                 175

Val Ala Val Asn Ala Phe Ile His Thr Val Met Tyr Ala His Tyr Phe
                    180                 185                 190

Arg Pro Phe Pro Lys Gln Phe Arg Pro Leu Ile Thr Gln Leu Gln Ile
                    195                 200                 205

Val Gln Phe Ile Phe Ser Ile Ala Ile His Thr Ala Ile Tyr Phe His
                210                 215                 220

Tyr Asp Cys Glu Pro Leu Val His Thr His Phe Tyr Glu Tyr Leu Thr
225                 230                 235                 240

Pro Tyr Tyr Ile Val Val Pro Phe Leu Phe Leu Phe Leu Asn Phe Tyr
                    245                 250                 255

Val Gln Gln Tyr Ile Leu Ala Pro Ser Lys Pro Lys Thr Lys Ser Ala
                260                 265                 270

<210> SEQ ID NO 17
<211> LENGTH: 220
<212> TYPE: PRT
<213> ORGANISM: Thraustochytrid sp. BICC
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid

<400> SEQUENCE: 17

Ser Gly Asn Ser Gly Arg Pro Cys Gln Asn Gly Ser Pro His Pro His
1               5                   10                  15

Phe Gln Leu Ile Ser Phe Leu Phe Ala Ala Ser Lys Val Trp Glu Trp
                20                  25                  30

Phe Asp Thr Val Leu Leu Ile Ile Lys Gly Asn Lys Leu Arg Phe Leu
            35                  40                  45

His Val Leu His His Ala Thr Thr Phe Trp Leu Tyr Ala Ile Asp His
        50                  55                  60

Ile Phe Leu Ser Ser Ile Lys Tyr Gly Val Ala Val Asn Ala Phe Ile
65                  70                  75                  80

His Thr Val Met Tyr Ala His Tyr Phe Arg Pro Phe Pro Lys Gln Phe
                85                  90                  95

Arg Pro Leu Ile Thr Gln Leu Gln Ile Val Gln Phe Ile Phe Ser Ile
                100                 105                 110
```

Ala Ile His Thr Ala Ile Tyr Phe His Tyr Asp Cys Glu Pro Leu Val
            115                 120                 125

His Thr His Phe Tyr Glu Tyr Leu Thr Pro Tyr Tyr Ile Val Val Pro
        130                 135                 140

Phe Leu Phe Leu Phe Leu Asn Phe Tyr Val Gln Gln Tyr Ile Leu Ala
145                 150                 155                 160

Pro Ser Lys Pro Lys Thr Lys Ser Ala Xaa Asp Glu Leu Ser Pro Thr
                165                 170                 175

Asp Ser Arg Leu Arg Phe His Xaa Gly Thr Ser Leu Val Xaa Ser Gln
            180                 185                 190

Thr Phe Ala Leu His Val Cys Glu Asp Gly Thr Leu Val Asn Glu Cys
        195                 200                 205

Met Asn Glu Tyr Glu Phe Ile Phe Arg Cys Val Phe
    210                 215                 220

<210> SEQ ID NO 18
<211> LENGTH: 182
<212> TYPE: PRT
<213> ORGANISM: Thraustochytrid sp. BICC

<400> SEQUENCE: 18

Thr Ile Arg Gln Ala Ile Leu Gly Gly Tyr Lys Val Phe Gly Asn Asp
1               5                   10                  15

Met Glu Lys Gly Asn Glu Ser His Ala Gln Gly Met Ser Arg Ile Val
            20                  25                  30

Tyr Val Phe Tyr Val Ser Lys Ala Tyr Glu Phe Leu Asp Thr Ala Ile
        35                  40                  45

Met Ile Leu Cys Lys Lys Phe Asn Gln Val Ser Phe Leu His Val Tyr
    50                  55                  60

His His Ala Thr Ile Phe Ala Ile Trp Trp Ala Ile Ala Lys Tyr Ala
65                  70                  75                  80

Pro Gly Gly Asp Ala Tyr Phe Ser Val Ile Leu Asn Ser Phe Val His
                85                  90                  95

Thr Val Met Tyr Ala Tyr Tyr Phe Ser Ser Gln Gly Phe Gly Phe
            100                 105                 110

Val Lys Pro Ile Lys Pro Tyr Ile Thr Thr Leu Gln Met Thr Gln Phe
        115                 120                 125

Met Ala Met Leu Val Gln Ser Leu Tyr Asp Tyr Leu Phe Pro Cys Asp
    130                 135                 140

Tyr Pro Gln Ala Leu Val Gln Leu Leu Gly Val Tyr Met Ile Thr Leu
145                 150                 155                 160

Leu Ala Leu Phe Gly Asn Phe Phe Val Gln Ser Tyr Leu Lys Lys Pro
                165                 170                 175

Lys Lys Ser Lys Thr Asn
            180

<210> SEQ ID NO 19
<211> LENGTH: 230
<212> TYPE: PRT
<213> ORGANISM: Murine

<400> SEQUENCE: 19

Ser Leu Arg Gly Ile Leu Thr Leu Tyr Asn Leu Ala Ile Thr Leu Leu
1               5                   10                  15

Ser Ala Tyr Met Leu Val Glu Leu Ile Leu Ser Ser Trp Glu Gly Gly
            20                  25                  30

```
Tyr Asn Leu Gln Cys Gln Asn Leu Asp Ser Ala Gly Glu Gly Asp Val
         35                  40                  45

Arg Val Ala Lys Val Leu Trp Trp Tyr Phe Ser Lys Leu Val Glu
 50                  55                  60

Phe Leu Asp Thr Ile Phe Phe Val Leu Arg Lys Lys Thr Asn Gln Ile
 65                  70                  75                  80

Thr Phe Leu His Val Tyr His Ala Ser Met Phe Asn Ile Trp Trp
                 85                  90                  95

Cys Val Leu Asn Trp Ile Pro Cys Gly Gln Ser Phe Phe Gly Pro Thr
                100                 105                 110

Leu Asn Ser Phe Ile His Ile Leu Met Tyr Ser Tyr Tyr Gly Leu Ser
                115                 120                 125

Val Phe Pro Ser Met His Lys Tyr Leu Trp Trp Lys Lys Tyr Leu Thr
                130                 135                 140

Gln Ala Gln Leu Val Gln Phe Val Leu Thr Ile Thr His Thr Leu Ser
145                 150                 155                 160

Ala Val Val Lys Pro Cys Gly Phe Pro Phe Gly Cys Leu Ile Phe Gln
                165                 170                 175

Ser Ser Tyr Met Met Thr Leu Val Ile Leu Phe Leu Asn Phe Tyr Ile
                180                 185                 190

Gln Thr Tyr Arg Lys Lys Pro Val Lys Lys Glu Leu Gln Glu Lys Glu
                195                 200                 205

Val Lys Asn Gly Phe Pro Lys Ala His Leu Ile Val Ala Asn Gly Met
                210                 215                 220

Thr Asp Lys Lys Ala Gln
225                 230

<210> SEQ ID NO 20
<211> LENGTH: 266
<212> TYPE: PRT
<213> ORGANISM: Danio rerio

<400> SEQUENCE: 20

Met Ser Val Leu Ala Leu Gln Glu Tyr Glu Phe Glu Arg Gln Phe Asn
 1               5                  10                  15

Glu Asp Glu Ala Ile Arg Trp Met Gln Glu Asn Trp Lys Lys Ser Phe
                20                  25                  30

Leu Phe Ser Ala Leu Tyr Ala Ala Cys Ile Leu Gly Gly Arg His Val
                35                  40                  45

Met Lys Gln Arg Glu Lys Phe Glu Leu Arg Lys Pro Leu Val Leu Trp
 50                  55                  60

Ser Leu Thr Leu Ala Ala Phe Ser Ile Phe Gly Ala Ile Arg Thr Gly
 65                  70                  75                  80

Gly Tyr Met Val Asn Ile Leu Met Thr Lys Gly Leu Lys Gln Ser Val
                 85                  90                  95

Cys Asp Gln Ser Phe Tyr Asn Gly Pro Val Ser Lys Phe Trp Ala Tyr
                100                 105                 110

Ala Phe Val Leu Ser Lys Ala Pro Glu Leu Gly Asp Thr Leu Phe Ile
                115                 120                 125

Val Leu Arg Lys Gln Lys Leu Ile Phe Leu His Trp Tyr His His Ile
                130                 135                 140

Thr Val Leu Leu Tyr Ser Trp Tyr Ser Tyr Lys Asp Met Val Ala Gly
145                 150                 155                 160

Gly Gly Trp Phe Met Thr Met Asn Tyr Leu Val His Ala Val Met Tyr
                165                 170                 175
```

```
Ser Tyr Tyr Ala Leu Arg Ala Ala Gly Phe Lys Ile Ser Arg Lys Phe
            180                 185                 190

Ala Met Phe Ile Thr Leu Thr Gln Ile Thr Gln Met Val Met Gly Cys
        195                 200                 205

Val Val Asn Tyr Leu Val Tyr Leu Trp Met Gln Gln Gly Gln Glu Cys
    210                 215                 220

Pro Ser His Val Gln Asn Ile Val Trp Ser Ser Leu Met Tyr Leu Ser
225                 230                 235                 240

Tyr Phe Val Leu Phe Cys Gln Phe Phe Glu Ala Tyr Ile Thr Lys
                245                 250                 255

Arg Lys Ser Asn Ala Ala Lys Lys Ser Gln
            260                 265
```

<210> SEQ ID NO 21
<211> LENGTH: 90
<212> TYPE: PRT
<213> ORGANISM: Artificial sequence
<220> FEATURE:
<223> OTHER INFORMATION: Chemically synthesized - consensus sequence

<400> SEQUENCE: 21

```
Ala Leu Tyr Phe Glu Asp Ile Ile Leu Ala Ile Ala Met Leu Leu Leu
1               5                   10                  15

Phe Ser Ile Thr Met Val Asn Leu Ala Cys Pro Ala Phe Phe Ser Lys
            20                  25                  30

Glu Asp Thr Leu Ile Ile Ile Lys Asn Lys Leu Phe Leu His His His
        35                  40                  45

Thr His Leu Ala Trp Met Met Asn Ile His Val Met Tyr Ala His Tyr
    50                  55                  60

Lys Phe Ile Thr Gln Ile Gln Ile Ile Tyr Ser His Leu Ile Leu
65                  70                  75                  80

Phe Leu Phe Asn Phe Pro Tyr Ile Lys Ala
                85                  90
```

<210> SEQ ID NO 22
<211> LENGTH: 262
<212> TYPE: PRT
<213> ORGANISM: Isochrysis galbana

<400> SEQUENCE: 22

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125
```

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Ile Leu Ala Pro Ser Lys
                245                 250                 255

Pro Lys Thr Lys Ser Ala
            260

<210> SEQ ID NO 23
<211> LENGTH: 94
<212> TYPE: PRT
<213> ORGANISM: Artificial sequence
<220> FEATURE:
<223> OTHER INFORMATION: Chemically sythesized - consensus sequence

<400> SEQUENCE: 23

Ala Leu Ala Ala Ala Ile Leu Leu Ile Gly Leu Leu Ala Tyr Ser
1               5                   10                  15

Leu Met Leu Ala Ala Leu Ala Leu Gly Ser Gly Ala Thr Asp Leu Phe
            20                  25                  30

Ala Phe Ser Lys Glu Trp Asp Thr Leu Ile Ile Lys Gly Lys Leu Phe
        35                  40                  45

Leu His His Trp Leu Tyr Ile Ile Met Asn Ala Phe Ile His Thr Ile
    50                  55                  60

Met Tyr His Tyr Phe Lys Pro Leu Ile Thr Leu Gln Ile Gln Phe Ile
65                  70                  75                  80

Ile Tyr Cys Phe Trp Tyr Val Leu Phe Phe Gln Ile Lys
                85                  90

<210> SEQ ID NO 24
<211> LENGTH: 304
<212> TYPE: PRT
<213> ORGANISM: Pavlova salina

<400> SEQUENCE: 24

Met Gly Pro Leu Ser Thr Leu Leu Ala Trp Met Pro Thr Trp Gly Glu
1               5                   10                  15

Phe Val Ala Gly Leu Thr Tyr Val Glu Arg Gln Gln Met Ser Glu Glu
            20                  25                  30

Leu Val Arg Ala Asn Lys Leu Pro Leu Ser Leu Ile Pro Glu Val Asp
        35                  40                  45

Phe Val Thr Ile Ala Ser Val Tyr Val Gly Asp His Trp Arg Ile Pro
    50                  55                  60

Phe Thr Ala Ile Ser Ala Tyr Leu Val Leu Ile Thr Leu Gly Pro Gln
65                  70                  75                  80

Leu Met Ala Arg Arg Pro Pro Leu Pro Ile Asn Thr Leu Ala Cys Leu

```
                     85                  90                  95
Trp Asn Phe Ala Leu Ser Leu Phe Ser Phe Val Gly Met Ile Val Thr
                100                 105                 110

Trp Thr Thr Ile Gly Glu Arg Leu Trp Lys Asn Gly Ile Glu Asp Thr
            115                 120                 125

Val Cys Gly His Pro Ile Phe Met Gly Tyr Gly Trp Ile Gly Tyr Val
        130                 135                 140

Met Leu Ala Phe Ile Trp Ser Lys Leu Phe Glu Leu Ile Asp Thr Val
145                 150                 155                 160

Phe Leu Val Ala Lys Lys Ala Asp Val Ile Phe Leu His Trp Tyr His
                165                 170                 175

His Val Thr Val Leu Leu Tyr Cys Trp His Ser Tyr Ala Val Arg Ile
            180                 185                 190

Pro Ser Gly Ile Trp Phe Ala Ala Met Asn Tyr Phe Val His Ala Ile
        195                 200                 205

Met Tyr Ala Tyr Phe Gly Met Thr Gln Ile Gly Pro Arg Gln Arg Lys
210                 215                 220

Leu Val Arg Pro Tyr Ala Arg Leu Ile Thr Thr Phe Gln Leu Ser Gln
225                 230                 235                 240

Met Gly Val Gly Leu Ala Val Asn Gly Leu Ile Ile Arg Tyr Pro Ser
                245                 250                 255

Ile Gly His His Cys His Ser Asn Lys Thr Asn Thr Ile Leu Ser Trp
            260                 265                 270

Ile Met Tyr Ala Ser Tyr Phe Val Leu Phe Ala Ala Leu Tyr Val Lys
        275                 280                 285

Asn Tyr Ile Phe Ser Lys Leu Lys Ser Pro Lys Arg Lys Lys Val Glu
    290                 295                 300

<210> SEQ ID NO 25
<211> LENGTH: 108
<212> TYPE: PRT
<213> ORGANISM: Artificial sequence
<220> FEATURE:
<223> OTHER INFORMATION: Chemically synthesized - consensus sequence

<400> SEQUENCE: 25

Met Gly Leu Ala Ser Ala Phe Phe Ser Glu Ile Ile Ser Ile Ser Leu
1               5                   10                  15

Ile Thr Leu Ala Met Arg Ile Leu Asn Ala Leu Leu Phe Ser Ile Thr
            20                  25                  30

Ile Ile Glu Cys Leu His Ile Phe Ser Lys Leu Phe Glu Asp Thr Val
        35                  40                  45

Leu Ile Lys Leu Phe Leu His His Thr Trp Trp Ile Ile Ser Trp
50                  55                  60

Ala Met Asn Phe Ile His Ile Met Tyr Ala His Phe Arg Lys Phe Leu
65                  70                  75                  80

Ile Thr Gln Ile Gln Ile Ala Ile Ile His Ser Ile Trp Ile Phe
            85                  90                  95

Leu Phe Tyr Val Asn Tyr Ile Ala Lys Pro Lys Lys
        100                 105

<210> SEQ ID NO 26
<211> LENGTH: 271
<212> TYPE: PRT
<213> ORGANISM: Thraustochytrium sp.

<400> SEQUENCE: 26
```

```
Met Met Glu Pro Leu Asp Arg Tyr Arg Ala Leu Ala Glu Leu Ala Ala
1               5                  10                  15

Arg Tyr Ala Ser Ser Ala Ala Phe Lys Trp Gln Val Thr Tyr Asp Ala
                20                  25                  30

Lys Asp Ser Phe Val Gly Pro Leu Gly Ile Arg Glu Pro Leu Gly Leu
            35                  40                  45

Leu Val Gly Ser Val Val Leu Tyr Leu Ser Leu Gln Ala Val Val Tyr
    50                  55                  60

Ala Leu Arg Asn Tyr Leu Gly Gly Leu Met Ala Leu Arg Ser Val His
65                  70                  75                  80

Asn Leu Gly Leu Cys Leu Phe Ser Gly Ala Val Trp Ile Tyr Thr Ser
                85                  90                  95

Tyr Leu Met Ile Gln Asp Gly His Phe Arg Ser Leu Glu Ala Ala Thr
            100                 105                 110

Cys Glu Pro Leu Lys His Pro His Phe Gln Leu Ile Ser Leu Leu Phe
            115                 120                 125

Ala Leu Ser Lys Ile Trp Glu Trp Phe Asp Thr Val Leu Leu Ile Val
    130                 135                 140

Lys Gly Asn Lys Leu Arg Phe Leu His Val Leu His His Ala Thr Thr
145                 150                 155                 160

Phe Trp Leu Tyr Ala Ile Asp His Ile Phe Leu Ser Ser Ile Lys Tyr
                165                 170                 175

Gly Val Ala Val Asn Ala Phe Ile His Thr Val Met Tyr Ala His Tyr
            180                 185                 190

Phe Arg Pro Phe Pro Lys Gly Leu Arg Pro Leu Ile Thr Gln Leu Gln
            195                 200                 205

Ile Val Gln Phe Ile Phe Ser Ile Gly Ile His Thr Ala Ile Tyr Trp
    210                 215                 220

His Tyr Asp Cys Glu Pro Leu Val His Thr His Phe Trp Glu Tyr Val
225                 230                 235                 240

Thr Pro Tyr Leu Phe Val Pro Phe Leu Ile Leu Phe Leu Asn Phe
                245                 250                 255

Tyr Leu Gln Gln Tyr Val Leu Ala Pro Ala Lys Thr Lys Lys Ala
            260                 265                 270

<210> SEQ ID NO 27
<211> LENGTH: 240
<212> TYPE: PRT
<213> ORGANISM: Artificial sequence
<220> FEATURE:
<223> OTHER INFORMATION: Chemically synthesized - consensus sequence

<400> SEQUENCE: 27

Met Leu Asp Arg Tyr Lys Ala Leu Ala Glu Ala Lys Tyr Ala Ser Ser
1               5                  10                  15

Ala Ala Phe Lys Trp Gln Val Thr Tyr Asp Ser Phe Val Gly Pro Ile
                20                  25                  30

Ile Glu Pro Leu Gly Leu Leu Val Gly Ser Leu Tyr Ala Val Tyr Leu
            35                  40                  45

Arg Tyr Leu Gly Gly Leu Met Ala Leu Arg His Asn Leu Gly Leu Cys
    50                  55                  60

Leu Phe Ser Gly Ala Val Trp Ile Tyr Thr Ser Tyr Leu Met Ile Gln
65                  70                  75                  80

Asp His Phe Ser Leu Glu Ala Ala Thr Cys Leu His Pro His Phe Gln
                85                  90                  95
```

```
Leu Ile Ser Leu Phe Ala Ser Lys Ile Trp Glu Trp Phe Asp Thr Val
            100                 105                 110
Leu Leu Ile Ile Lys Gly Asn Lys Leu Arg Phe Leu His Val Leu His
        115                 120                 125
His Ala Thr Thr Phe Trp Leu Tyr Ala Ile Asp His Ile Phe Leu Ser
    130                 135                 140
Ser Ile Lys Tyr Gly Val Ala Val Asn Ala Phe Ile His Thr Val Met
145                 150                 155                 160
Tyr Ala His Tyr Phe Arg Pro Phe Pro Lys Arg Pro Leu Ile Thr Gln
                165                 170                 175
Leu Gln Ile Val Gln Phe Ile Phe Ser Ile Ala Ile His Thr Ala Ile
            180                 185                 190
Tyr Phe His Tyr Asp Cys Glu Pro Leu Val His Thr His Phe Trp Glu
        195                 200                 205
Tyr Leu Thr Pro Tyr Val Val Pro Phe Leu Leu Phe Leu Asn Phe Tyr
    210                 215                 220
Leu Gln Gln Tyr Ile Leu Ala Pro Ser Lys Pro Lys Thr Lys Ser Ala
225                 230                 235                 240
```

ELONGASE GENE AND USES THEREOF

CROSS-REFERENCE TO RELATED APPLICATION

This application is a continuation-in-part of U.S. patent application Ser. No. 11/601,544, filed on Nov. 17, 2006 now abandoned.

BACKGROUND OF THE INVENTION

1. Technical Field

The subject invention relates to the identification of a gene involved in the elongation of long-chain polyunsaturated fatty acids (i.e., "elongase") and to uses thereof. In particular, the elongase enzyme is utilized in the conversion of one fatty acid to another. For example, elongase catalyzes the conversion of γ-linolenic acid (GLA, 18:3n-6) to dihomo-γ-linolenic acid (DGLA, 20:3n-6) and the conversion of stearidonic acid (STA, 18:4n-3) to eicosatetraenoic acid (ETA, 20:4n-3). Elongase also catalyzes the conversion of arachidonic acid (AA, 20:4n-6) to adrenic acid (ADA, 22:4n-6), the conversion of eicosapentaenoic acid (EPA, 20:5n-3) to ω3-docosapentaenoic acid (22:5n-3), the conversion of linoleic acid (LA, 8:2n-6) to eicosadienoic acid (EDA, 20:2n6), and the conversion of α-linolenic acid (ALA, 18:3n-3) to eicosatrienoic acid (ETrA, 20:3n-3). ALA, for example, may be utilized in the production of other polyunsaturated fatty acids (PUFAs), such as ETrA. ETrA may then be converted to ETA by a Δ8-desaturase. ETA may then be utilized in the production of other polyunsaturated fatty acids, such as EPA, which may be added to pharmaceutical compositions, nutritional compositions, animal feeds, as well as other products such as cosmetics.

2. Background Information

The elongases which have been identified in the past differ in terms of the substrates upon which they act. Furthermore, they are present in both animals and plants. Those found in mammals have the ability to act on saturated, monounsaturated and polyunsaturated fatty acids. In contrast, those found in plants are specific for saturated or monounsaturated fatty acids. Thus, in order to generate polyunsaturated fatty acids in plants, there is a need for a PUFA-specific elongase.

In both plants and animals, the elongation process is believed to be the result of a four-step mechanism (Lassner et al., *The Plant Cell* 8:281-292 (1996)). CoA is the acyl carrier. Step one involves condensation of malonyl-CoA with a long-chain acyl-CoA to yield carbon dioxide and a β-ketoacyl-CoA in which the acyl moiety has been elongated by two carbon atoms. Subsequent reactions include reduction to β-hydroxyacyl-CoA, dehydration to an enoyl-CoA, and a second reduction to yield the elongated acyl-CoA. The initial condensation reaction is not only the substrate-specific step but also the rate-limiting step.

As noted previously, elongases, more specifically, those which utilize PUFAs as substrates, are critical in the production of long-chain polyunsaturated fatty acids which have many important functions. For example, PUFAs are important components of the plasma membrane of a cell where they are found in the form of phospholipids. They also serve as precursors to mammalian prostacyclins, eicosanoids, leukotrienes and prostaglandins. Additionally, PUFAs are necessary for the proper development of the developing infant brain as well as for tissue formation and repair. In view of the biological significance of PUFAs, attempts are being made to produce them, as well as intermediates leading to their production, efficiently.

A number of enzymes are involved in PUFA biosynthesis including elongases (ELO) (FIG. 1). For example, linoleic acid (LA, 18:2n-6) is produced from oleic acid (OA, 18:1n-9) by a Δ12-desaturase. Eicosadienoic acid (EDA, 20:2n-6) is produced from linoleic acid (LA, 18:2n-6) by a Δ9-elongase. Dihomo-γ-linolenic acid (DGLA, 20:3n-6) is produced from eicosadienoic acid (EDA, 20:2n-6) by a Δ8-desaturase. Arachidonic acid (AA, 20:4n-6) is produced from dihomo-γ-linolenic acid (DGLA, 20:3n-6) by a Δ5-desaturase.

It must be noted that animals cannot desaturate beyond the Δ9 position and therefore cannot convert oleic acid (OA, 18:1n-9) into linoleic acid (LA, 18:2n-6). Likewise, α-linolenic acid (ALA, 18:3n-3) cannot be synthesized by mammals, since they lack Δ15-desaturase activity. However, α-linolenic acid can be converted to stearidonic acid (STA, 18:4n-3) by a Δ6-desaturase (see PCT publication WO 96/13591; see also U.S. Pat. No. 5,552,306), followed by elongation to eicosatetraenoic acid (ETA, 20:4n-3) in mammals and algae. This polyunsaturated fatty acid (i.e., ETA, 20:4n-3) can then be converted to eicosapentaenoic acid (EPA, 20:5-3) by a Δ5-desaturase. Other eukaryotes, including fungi and plants, have enzymes which desaturate at carbons 12 (see PCT publication WO 94/11516 and U.S. Pat. No. 5,443,974) and 15 (see PCT publication WO 93/11245). The major polyunsaturated fatty acids of animals therefore are either derived from diet and/or from desaturation and elongation of linoleic acid or α-linolenic acid. In view of the inability of mammals to produce these essential long-chain fatty acids, it is of significant interest to isolate genes involved in PUFA biosynthesis from species that naturally produce these fatty acids and to express these genes in a microbial, plant or animal system which can be altered to provide production of commercial quantities of one or more PUFAs. Consequently, there is a definite need for elongase enzymes, the genes encoding the enzymes, as well as recombinant methods of producing the enzymes.

In view of the above discussion, a definite need exists for oils containing levels of PUFAs beyond those naturally present as well as those enriched in novel PUFAs. Such oils can only be made by isolation and expression of elongase genes.

One of the most important long-chain PUFAs is eicosapentaenoic acid (EPA). EPA is found in fungi and also in marine oils. Docosahexaenoic acid (DHA) is another important long-chain PUFA. DHA is most often found in fish oil and can also be purified from mammalian brain tissue. Arachidonic acid (AA) is a third important long-chain PUFA. AA is found in filamentous fungi and can also be purified from mammalian tissues including the liver and the adrenal glands.

AA, EPA and/or DHA, for example, can be produced via either the alternate delta 8 pathway or the conventional delta 6 pathway (FIG. 1). Elongase, which are active on substrate fatty acids in the conventional delta 6 pathway for the production of long-chain PUFAs, particularly AA, EPA and DHA, have previously been identified. The conventional delta 6 pathway for converting LA to DGLA and ALA to ETA utilizes the Δ6-desaturase enzyme to convert LA to GLA, and ALA to STA, and the Δ6-elongase enzyme to convert GLA to DGLA, and STA to ETA. However, in certain instances, the alternate delta 8 pathway may be preferred over the conventional delta 6 pathway. For example, if particular residual omega-6 or omega-3 fatty acid intermediates, such as GLA or STA, are not desired during production of DGLA, ETA, AA, EPA, ω3-docosapentaenoic acid, ω6-docosapentaenoic acid, ADA and/or DHA, the alternate delta 8 pathway may be used as an alternative to the conventional delta 6 pathway, to bypass GLA and STA formation.

In the present invention, a new source of Δ9-elongase has been identified for the production of long-chain PUFAs, in particular DGLA, ETA, AA, EPA, ω3-docosapentaenoic acid, ω6-docosapentaenoic acid, ADA and/or DHA. Such oils can be made, in part, by isolation and expression of the Δ9-elongase gene. The Δ9-elongase enzyme of the present invention converts, for example, LA to EDA. The production of DGLA from EDA, and AA from DGLA, is then catalyzed by a Δ8-desaturase and a Δ5-desaturase, respectively.

The search for a long-chain PUFA-specific Δ9-elongase in Thraustochytrid sp. began based upon a review of the homologies shared between this gene and by expression screening for PUFA-elongase activity.

All patents and publications referred to herein are hereby incorporated in their entirety by reference.

SUMMARY OF THE INVENTION

The present invention encompasses an isolated nucleic acid molecule or fragment thereof comprising or complementary to a nucleotide sequence encoding a polypeptide or protein having elongase activity and having at least 86% identity or similarity to an amino acid sequence comprising SEQ ID NO:2 (FIG. 3).

Furthermore, the present invention includes an isolated nucleotide sequence or fragment comprising or complementary to at least 86% of a nucleotide sequence comprising SEQ ID NO:1 (FIG. 2). In particular, the isolated sequence may be represented by SEQ ID NO:1. The sequence encodes a functionally active elongase which utilizes a polyunsaturated fatty acid as a substrate.

The nucleotide sequence may be from a fungus of, for example, the family Thraustochytrids (or Thraustochytriidae), and may specifically be isolated from, for example, a Thraustochytrid sp., from *Thraustochytrium aureum* 7087, or from Thraustochytrid sp. BICC 7087.

The present invention also includes a purified polypeptide or protein encoded by the above nucleotide sequence as well as a purified polypeptide or protein which elongates polyunsaturated fatty acids containing unsaturation at the carbon 9 position and has at least 86% amino acid identity or similarity to the amino acid sequence of the purified protein encoded by the above nucleotide sequence.

Furthermore, the present invention also encompasses a method of producing a Δ9-elongase enzyme. This method comprises the steps of: a) isolating the nucleotide sequence comprising SEQ ID NO:1 (FIG. 2); b) constructing a vector comprising: i) the isolated nucleotide sequence operably linked to ii) a promoter or some type of regulatory sequence; and c) introducing the vector into a host cell for a time and under conditions sufficient for expression of the Δ9-elongase enzyme, as appropriate. The host cell may be, for example, a eukaryotic cell or a prokaryotic cell. In particular, the prokaryotic cell may be, for example, *Escherichia coli*, cyanobacteria or *Bacillus subtilis*. The eukaryotic cell may be, for example, a mammalian cell, an insect cell, a plant cell or a fungal cell. The fungal cell may be, for example, *Saccharomyces* spp., *Candida* spp., *Lipomyces* spp., *Yarrowia* spp., *Aspergillus* spp., *Penicillium* spp., *Neurospora* spp., *Kluyveromyces* spp., *Hansenula* spp., *Trichoderma* spp., or *Pichia* spp. In particular, the fungal cell may be a yeast cell such as, for example, *Saccharomyces* spp., *Candida* spp., *Hansenula* spp. and *Pichia* spp. The yeast cell may also be, for example, *Saccharomyces cerevisiae*.

Additionally, the present invention also encompasses a vector comprising: a) a nucleotide sequence as represented by SEQ ID NO:1 (FIG. 2), operably linked to b) a promoter or regulatory sequence. The invention also includes a host cell comprising this vector. The host cell may be, for example, a eukaryotic cell or a prokaryotic cell. Suitable eukaryotic cells and prokaryotic cells are as defined above.

Moreover, the present invention also includes a plant cell, plant seed, plant or plant tissue comprising the above vector, wherein expression of the nucleotide sequence of the vector results in production of at least one polyunsaturated fatty acid by the plant cell, plant or plant tissue. The polyunsaturated fatty acid may be, for example, selected from the group consisting of EDA and ETrA. The invention also includes one or more plant oils or fatty acids expressed by the above plant cell, plant seed, plant or plant tissue.

Additionally, the present invention also encompasses a transgenic plant comprising the above vector, wherein expression of the nucleotide sequence of the vector results in production of at least one polyunsaturated fatty acid in seeds of the transgenic plant.

Also, the invention includes a mammalian cell comprising the above vector wherein expression of the nucleotide sequence of the vector results in production of altered levels of, for example, EDA and/or ETrA when the cell is grown in a culture media comprising a fatty acid selected from the group consisting of for example, LA and ALA.

It should also be noted that the present invention encompasses a transgenic, non-human mammal whose genome comprises a DNA sequence encoding a Δ9-elongase operably linked to a promoter or regulatory sequence. The DNA sequence may be represented by SEQ ID NO:1 (FIG. 2). The present invention also includes a fluid (e.g., milk) produced by the transgenic, non-human mammal wherein the fluid comprises a detectable level of Δ9-elongase.

Additionally, the present invention includes a method (i.e. "first" method") for producing a polyunsaturated fatty acid comprising the steps of: a) isolating the nucleotide sequence represented by SEQ ID NO:1 (FIG. 2); b) constructing a vector comprising the isolated nucleotide sequence; c) introducing the vector into a host cell under time and conditions sufficient for expression of Δ9-elongase enzyme; and d) exposing the expressed Δ9-elongase enzyme to a substrate polyunsaturated fatty acid in order to convert the substrate to a product polyunsaturated fatty acid. The "substrate" polyunsaturated fatty acid is, for example, LA and ALA, and the "product" polyunsaturated fatty acid is, for example, EDA or ETrA, respectively. This method may further comprise the step of exposing the product polyunsaturated fatty acid to at least one desaturase in order to convert the product polyunsaturated fatty acid to another polyunsaturated fatty acid (i.e., "second" method). In this method containing the additional step (i.e., "second" method), the product polyunsaturated fatty acid may be, for example, EDA or ETrA, the "another" polyunsaturated fatty acid may be, for example, DGLA or ETA, respectively, and the at least one desaturase may be, for example, Δ8-desaturase. The method containing the additional step (i.e., "second" method) may further comprise a step of exposing the another polyunsaturated fatty acid to at least one additional desaturase in order to convert the another polyunsaturated fatty acid to an additional polyunsaturated fatty acid (i.e., "third" method). In this method containing the additional step (i.e., "third" method), the another polyunsaturated fatty acid may be, for example, DGLA or ETA, the "additional" polyunsaturated fatty acid may be, for example, AA or EPA, respectively, and the at least one additional desaturase may be, for example, Δ5-desaturase. The method containing the additional step (i.e., "third" method) may further comprise a step of exposing the additional polyunsaturated fatty acid to at least one additional desaturase and/or at least one additional elongase in order to in order to convert the additional polyunsaturated fatty acid to a final polyunsaturated fatty acid (i.e., "fourth" method). In this method containing the additional step (i.e., "fourth" method), the additional polyunsaturated fatty acid may be, for example, AA or EPA, and the "final" polyunsaturated fatty acid may be, for example, ω3-docosapentaenoic acid, ω6-docosapentaenoic acid, ADA or DHA.

The present invention also encompasses a composition comprising at least one polyunsaturated fatty acid selected from the group consisting of the product polyunsaturated fatty acid produced according to the methods described above, the another polyunsaturated fatty acid produced according to the methods described above, the additional polyunsaturated fatty acid produced according to the methods described above, and the final polyunsaturated fatty acid produced according to the methods described above. The product polyunsaturated fatty acid may be, for example, EDA or ETrA. The another polyunsaturated fatty acid may be, for example, DGLA or ETA. The additional polyunsaturated fatty acid may be, for example, AA or EPA. The final polyunsaturated fatty acid may be, for example, ω3-docosapentaenoic acid, ω6-docosapentaenoic acid, ADA or DHA. The composition may be, for example, a nutritional composition such as an infant formula, a dietary supplement or a dietary substitute and may be administered to a human or an animal and may be administered enterally or parenterally. The nutritional composition may further comprise at least one macronutrient selected from the group consisting of coconut oil, soy oil, canola oil, monoglycerides, diglycerides, triglycerides, glucose, edible lactose, electrodialysed whey, electrodialysed skim milk, milk whey, soy protein, protein hydrolysates, sunflower oil, safflower oil, corn oil, and flax oil. It may also comprise at least one vitamin selected from the group consisting of Vitamins A, C, D, E, and B complex and at least one mineral selected from the group consisting of calcium magnesium, zinc, manganese, sodium, potassium, phosphorus, copper, chloride, iodine, selenium and iron.

The present invention also includes a pharmaceutical composition comprising 1) at least one polyunsaturated fatty acid (PUFA) selected from the group consisting of the "product" PUFA produced according to the methods described above, the "another" PUFA produced according to the methods described above, the "additional" PUFA produced according to the methods described above, or the "final" PUFA produced according to the methods described above and 2) a pharmaceutically acceptable carrier. The composition may be administered to a human or an animal. It may also further comprise at least one element selected from the group consisting of a vitamin, a mineral, a salt, a carbohydrate, an amino acid, a free fatty acid, a preservative, an excipient, an anti-histamine, a growth factor, an antibiotic, a diluent, a phospholipid, an antioxidant, and a phenolic compound. It may be administered enterally, parenterally, topically, rectally, intramuscularly, subcutaneously, intradermally, or by any other appropriate means.

Additionally, the present invention encompasses an animal feed or cosmetic comprising at least one PUFA selected from the group consisting of the product PUFA produced according to the methods described above, the another PUFA produced according to the methods described above, the additional PUFA produced according to the methods described above and the final PUFA produced according to the methods described above. These PUFAs have been listed above and are exemplified in FIG. 1. Additionally, the present invention encompasses a method of preventing or treating a condition caused by insufficient intake of polyunsaturated fatty acids comprising administering to the patient the compositions above in an amount sufficient to effect prevention or treatment.

It should also be noted that each nucleotide and amino acid sequence referred to herein has been assigned a particular sequence identification number. The Sequence Listing (which is found herein) lists each such sequence and its corresponding number.

BRIEF DESCRIPTION OF THE DRAWINGS

FIG. 2 illustrates the nucleotide sequence encoding Δ9-elongase (pRAT-5A1) of Thraustochytrid sp. BICC 7087 (SEQ ID NO:1).

FIG. 3 illustrates the translated amino acid sequence of Δ9-elongase (pRAT-5A1) of Thraustochytrid sp. BICC 7087 (SEQ ID NO:2).

FIG. 4 illustrates the amino acid sequence identity between the '660R1' EST clone (SEQ ID NO: 17), mouse elongase MEL04 (SEQ ID NO: 19), and Thraustochytrid sp. BICC elongase TELO1 (SEQ ID NO: 18).

FIG. 6 illustrates the PUFA elongase activity of the Δ9-elongase gene (pRAT-5A1) from Thraustochytrid sp. BICC 7087.

FIG. 7 illustrates the amino acid sequence identity between elongase-encoded proteins from *Danio rerio* (SEQ ID NO: 20) and pRAT-5A1 (SEQ ID NO: 2).

FIG. 8 illustrates the amino acid sequence identity between Δ9-elongase-encoded proteins from *Isochrysis galbana* (SEQ ID NO: 22) and pRAT-5A1 (SEQ ID NO: 2).

FIG. 9 illustrates the amino acid sequence identity between Δ9-elongase-encoded proteins from *Pavlova salina* (SEQ ID NO: 24) and pRAT-5A1 (SEQ ID NO: 2).

FIG. 10 illustrates the amino acid sequence identity between proteins encoded by *Thraustochytrium* sp. FJN-10 (SEQ ID NO: 26) and pRAT-5A1 (SEQ ID NO: 2).

FIG. 11 illustrates the amino acid sequence alignment of proteins encoded by pRAT-5A1 (SEQ ID NO:2), pRAT-5A1 mutant 1 (SEQ ID NO: 5) and pRAT-5A1 mutant 2 (SEQ ID NO:6)

FIG. 12 illustrates the PUFA elongase activity of the Δ9-elongase gene (pRAT-5A1) from Thraustochytrid sp. BICC 7087, the pRAT-5A1 mutant 1 and the pRAT-5A1 mutant 2.

FIG. 13 illustrates the amino acid sequence alignment of proteins encoded by pRAT-5A1 (SEQ ID NO:2), pRAT-5A11 (SEQ ID NO: 15) and pRAT-5B (SEQ ID NO:16).

FIG. 15 illustrates the fatty acid profile of transgenic seeds expressing pRAT-5A1 versus non-transgenic seeds.

DETAILED DESCRIPTION OF THE INVENTION

Figure 1:
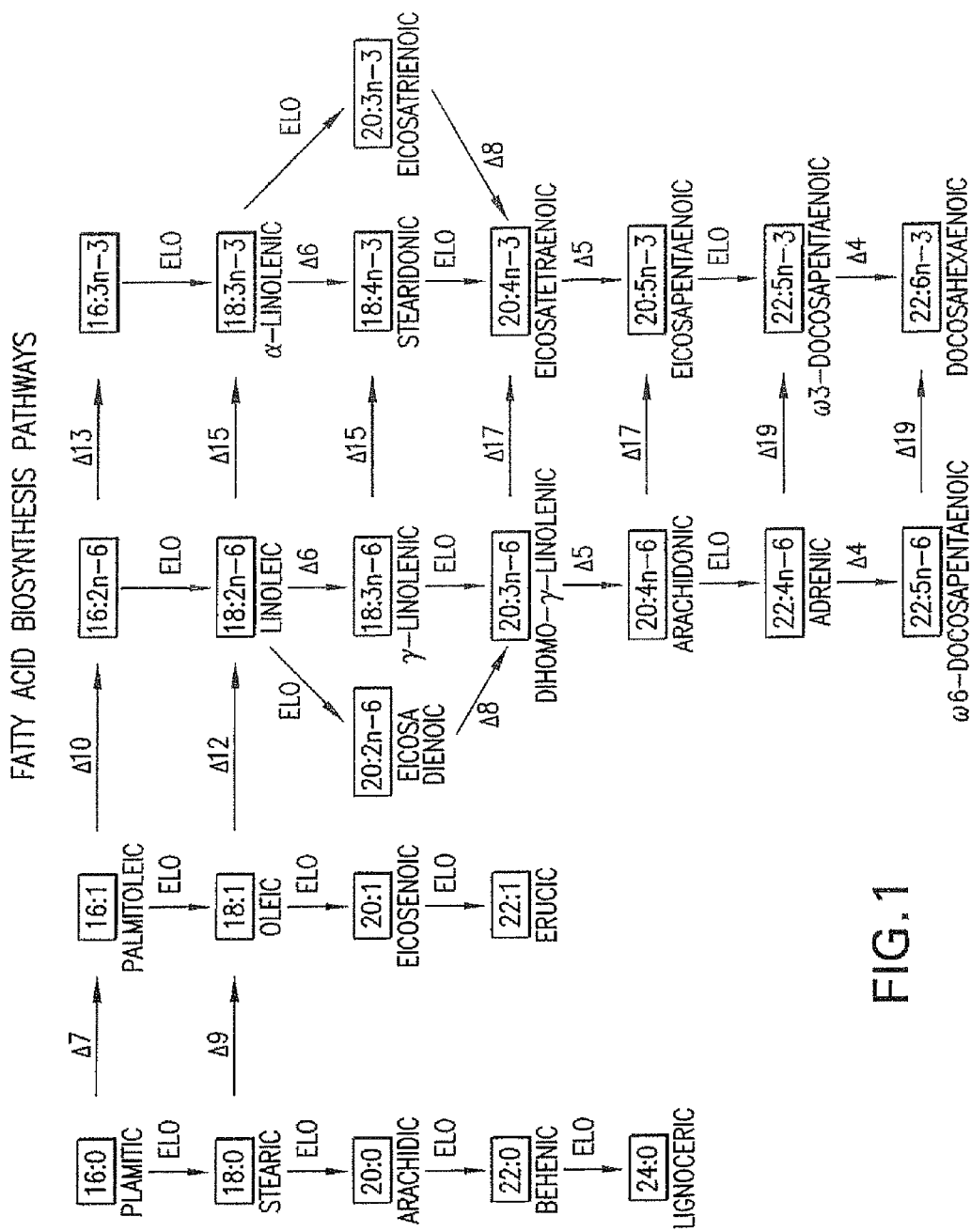
FIG. 1 illustrates the fatty acid biosynthetic pathway and the role of Δ9-elongase in this pathway.

The subject invention relates to the nucleotide and translated amino acid sequences of a Δ9-elongase gene from Thraustochytrid sp., for example, *Thraustochytrium aureum*

7087, or Thraustochytrid sp. BICC 7087. Furthermore, the subject invention also includes uses of the gene and of the enzyme encoded by the gene. For example, the gene and corresponding enzyme may be used in the production of polyunsaturated fatty acids such as, for instance, EDA, EtrA, DGLA, ETA, AA, EPA, ω3-docosapentaenoic acid, ω6-docosapentaenoic acid, ADA and/or DHA which may be added to pharmaceutical compositions, nutritional compositions and to other valuable products.

The Δ9-Elongase Gene and Enzyme Encoded Thereby

As noted above, the enzyme encoded by the Δ9-elongase gene of the present invention is essential in the production, via the alternate delta 8 pathway, of long-chain polyunsaturated fatty acids, having a length greater than 20 carbons. The nucleotide sequence of the isolated Thraustochytrid sp. BICC 7087 Δ9-elongase gene (pRAT-5A1) is shown in FIG. 2, and the amino acid sequence of the corresponding purified protein is shown in FIG. 3.

The conversion of LA to DGLA and ALA to ETA using a Δ9-elongase enzyme and a Δ8-desaturase enzyme is referred to as the alternate delta 8 pathway. The conventional delta 6 pathway for converting LA to DGLA and ALA to ETA utilizes a Δ6-desaturase enzyme to convert LA to GLA, and ALA to STA, and a Δ6-elongase gene to convert GLA to DGLA, and STA to ETA, respectively. In either pathway, the production of AA or EPA is then catalyzed by, for example, a Δ5-desaturase. DHA, for example, may be produced upon the conversion of EPA to ω3-docosapentaenoic acid, and ω3-docosapentaenoic acid to DHA, utilizing, for example, a C20-elongase and a Δ4-desaturase, respectively.

Although, for example, DGLA, ETA, AA, EPA, ω3-docosapentaenoic acid, ω6-docosapentaenoic acid, ADA and/or DHA can be produced via either the alternate delta 8 pathway or the conventional delta 6 pathway, in certain instances, the alternate delta 8 pathway may be preferred over the conventional delta 6 pathway. For example, if particular residual omega-6 or omega-3 fatty acid intermediates, such as GLA or STA, are not desired during production of DGLA, ETA, AA, EPA, ω3-docosapentaenoic acid, ω6-docosapentaenoic acid, ADA and/or DHA, the alternate delta 8 pathway may be used as an alternative to the conventional delta 6 pathway, to bypass GLA and STA formation.

As discussed above, Δ9-elongase is a necessary enzyme in the alternate delta 8 pathway. EPA, for example, cannot be synthesized via the alternate delta 8 pathway without the Δ9-elongase gene and enzyme encoded thereby. The isolated Δ9-elongase enzyme of the present invention converts, for example, ALA to ETrA. The production of ETA from ETrA, and EPA from ETA, is then catalyzed by, for example, a Δ8-desaturase and a Δ5-desaturase, respectively. As a result of using the alternate delta 8 pathway, the intermediate GLA and STA fatty acids are bypassed.

It should be noted that the present invention also encompasses nucleotide sequences (and the corresponding encoded proteins) having sequences comprising or complementary to at least 86%, preferably at least 88%, more preferably at least 90%, more preferably at least 95% and most preferably at least 97% of the nucleotides in sequence (i.e., having sequence identity to) SEQ ID NO:1 (i.e., the nucleotide sequence of the Δ9-elongase gene of Thraustochytrid sp. BICC 7087). (All integers between 80% and 100% are also considered to be within the scope of the present invention with respect to percent identity.) Such sequences may be from human sources as well as other non-human sources (e.g., C. elegans or mouse).

Furthermore, the present invention also encompasses fragments and derivatives of the nucleotide sequence of the present invention (i.e., SEQ ID NO:1 (shown in FIG. 2)), as well as of the sequences from other sources, and having the above-described complementarity or correspondence. Functional equivalents of the above-sequences (i.e., sequences having Δ9-elongase) are also encompassed by the present invention.

It should also be noted that the present invention also encompasses nucleotide sequences or fragments thereof encoding a polypeptide having elongase activity, wherein the amino acid sequence of said polypeptide has at least 86%, preferably at least 88%, more preferably at least 90%, more preferably at least 95% and most preferably at least 97% sequence identity to the amino acid sequence comprising SEQ ID NO:2. (All integers between 80% and 100% are also considered to be within the scope of the present invention with respect to percent identity.) Such sequences may be from human sources as well as other non-human sources (e.g., C. elegans or mouse).

The invention also includes a purified polypeptide which elongates polyunsaturated fatty acids containing unsaturation at the carbon 9 position and has at least 86% amino acid similarity or identity, preferably at least 88% similarity or identity, more preferably at least 90% similarity or identity, more preferably at least 95% similarity or identity, and most preferably at least 97% similarity or identity to the amino acid sequence (i.e., SEQ ID NO:2 (shown in FIG. 3)), polypeptide or protein of the above-noted proteins which are, in turn, encoded by the above-described nucleotide sequences. All integers between 80-100% similarity or identity are also included within the scope of the invention.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments. "Percentage of sequence identity" is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912, 120.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity" between two amino acid sequences is defined as the presence of a series of exactly alike or invariant amino acid residues in both sequences.)

The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which encodes PUFA elongase activity and that is hybridizable, under moderately stringent conditions, to a nucleic acid having a nucleotide sequence comprising or complementary to the nucleotide sequence comprising SEQ ID NO:1 (shown in FIG. 2). A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid molecule in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid molecules wherein changes in one or more nucleotide bases does not affect the ability of the nucleic acid molecule to mediate gene expression or produce a certain phenotype. These terms also refer to modifications of the nucleic acid molecules of the instant invention such as deletion or insertion of one or more nucleotides that do not substantially alter the functional properties of the resulting nucleic acid molecule relative to the initial, unmodified molecule. It is therefore understood, as those skilled in the art will appreciate, that the invention encompasses more than the specific exemplary sequences.

"Gene" refers to a nucleic acid molecule that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid molecules that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters." New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA molecules of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymeras-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow molecule of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid molecule so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid molecule into a genome of a host organism, including both nuclear and organellar genomes, resulting in genetically stable inheritance. In contrast, "transient transformation" refers to the transfer of a nucleic acid molecule into the nucleus, or DNA-containing organelle, of a host organism resulting in gene expression without integration or stable inheritance. Host organisms containing the transformed nucleic acid molecules are referred to as "transgenic" organisms. The preferred method of cell transformation of rice, corn and other monocots is the use of particle-accelerated or "gene gun" transformation technology (Klein et al., (1987) *Nature (London)* 327:70-73; U.S. Pat. No. 4,945,050), or an *Agrobacterium*-mediated method using an appropriate Ti plasmid containing the transgene (Ishida Y. et al., 1996, Nature Biotech. 14:745-750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263-273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid molecules of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Production of the Δ9-Elongase Enzyme

Once the gene encoding the elongase enzyme has been isolated, it may then be introduced into either a prokaryotic or eukaryotic host cell through the use of a vector or construct. The vector, for example, a bacteriophage, cosmid, or plasmid, may comprise the nucleotide sequence encoding the Δ9-elongase enzyme, as well as any regulatory sequence (e.g., promoter) which is functional in the host cell and is able to elicit expression of the elongase encoded by the nucleotide sequence. The regulatory sequence is in operable association with or operably linked to the nucleotide sequence. (As noted above, regulatory is said to be "operably linked" with a coding sequence if the regulatory sequence affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g. the poly-A signal of SV40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual*, $2^{nd}$ ed., Vol. 1-3, ed. Sambrook et al., Cold Spring Harbor Laboratory Press (1989)). The host cell is then cultured under suitable conditions permitting expression of the genes leading to the production of the desired PUFA, which is then recovered and purified.

Examples of suitable prokaryotic host cells include, for example, bacteria such as *Escherichia coli, Bacillus subtilis* as well as cyanobacteria such as *Spirulina* spp. (i.e., blue-green algae). The eukaryotic cell may be, for example, a mammalian cell, an insect cell, a plant cell or a fungal cell. The fungal cell may be, for example, *Saccharomyces* spp., *Candida* spp., *Lipomyces* spp., *Yarrowia* spp., *Aspergillus* spp., *Penicillium* spp., *Neurospora* spp., *Kluyveromyces* spp., *Hansenula* spp., *Trichoderma* spp., or *Pichia* spp. In particular, the fungal cell may be a yeast cell such as, for example, *Saccharomyces* spp., *Candida* spp., *Hansenula* spp. and *Pichia* spp. The yeast cell may also be *Saccharomyces cerevisiae*.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the Δ9-elongase enzyme and ultimately the PUFA(s) of interest. More specifically, once the above-described construct is created, it may be inserted into the pronucleus of an embryo. The embryo may then be implanted into a recipient female. Alternatively, a nuclear transfer method could also be utilized (Schnieke et al., Science 278:2130-2133 (1997)). Gestation and birth are then permitted (see, e.g., U.S. Pat. Nos. 5,750,176 and 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene encoding the desired desaturase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of a elongase polypeptide, functional transcriptional and translational initiation and termination regions are operably linked to the DNA encoding the elongase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379. Alternatively, the expressed protein can be an enzyme which produces a product which may be incorporated, either directly or upon further modifications, into a fluid fraction from the host plant. Expression of a elongase gene, or antisense elongase transcripts, can alter the levels of specific PUFAs, or derivatives thereof, found in plant parts and/or plant tissues. The elongase polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)) or plant tissue may also be utilized as a host or host cell, respectively, for expression of the elongase enzyme which may, in turn, be utilized in the production of polyunsaturated fatty acids. More specifically, desired PUFAS can be expressed in seed. Methods of isolating seed oils are known in the art. Thus, in addition to providing a source for PUFAs, seed oil components may be manipulated through the expression of the elongase gene, as well as perhaps desaturase genes and other elongase genes, in order to provide seed oils that can be added to nutritional compositions, pharmaceutical compositions, animal feeds and cosmetics. Once again, a vector which comprises a DNA sequence encoding the elongase operably linked to a promoter, will be introduced into the plant tissue or plant for a time and under conditions sufficient for expression of the elongase gene. The vector may also comprise one or more genes that encode other enzymes, for example, elongase, Δ4-desaturase, Δ5-desaturase, Δ6-desaturase, Δ10-desaturase, Δ12-desaturase, Δ15-desaturase, Δ17-desaturase, and/or Δ19-desaturase. The plant tissue or plant may produce the relevant substrate upon which the enzymes act or a vector encoding enzymes which produce such substrates may be introduced into the plant tissue, plant cell or plant. In addition, substrate may be sprayed on plant tissues expressing the appropriate enzymes. Using these various techniques, one may produce PUFAs by use of a plant cell, plant tissue or plant. It should also be noted that the invention also encompasses a transgenic plant comprising the above-described vector, wherein expression of the nucleotide sequence of the vector results in production of a polyunsaturated fatty acid in, for example, the seeds of the transgenic plant.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. Nos. 5,004,863, 5,159,135, and 5,518,908); soybean (U.S. Pat. Nos. 5,569,834, and 5,416,011, McCabe et. al., *BioTechnology* 6:923 (1988), Christou et al., *Plant Physiol.* 87:671-674 (1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); *Zea mays* (Rhodes et al., *Science* 240:204 (1988), Gordon-Kamm et al., *Plant Cell* 2:603-618 (1990), Fromm et al., *BioTechnology* 8:833 (1990), Koziel et al., *BioTechnology* 11: 194, (1993), Armstrong et al., *Crop Science* 35:550-557 (1995)); oat (Somers et al., *BioTechnol-* ogy 10: 15 89 (1992)); orchard grass (Horn et al., *Plant Cell Rep.* 7:469 (1988)); rice (Toriyama et al., *TheorAppl. Genet.* 205:34, (1986); Part et al., *Plant Mol. Biol.* 32:1135-1148, (1996); Abedinia et al., *Aust. J. Plant Physiol.* 24:133-141 (1997); Zhang and Wu, *Theor. Appl. Genet.* 76:835 (1988); Zhang et al. *Plant Cell Rep.* 7:379, (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *BiolTechnology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

The substrates which may be produced by the host cell either naturally or transgenically, as well as the enzymes which may be encoded by DNA sequences present in the vector which is subsequently introduced into the host cell, are shown in FIG. 1.

In view of the above, the present invention encompasses a method of producing the Δ9-longase enzyme comprising the steps of: 1) isolating the nucleotide sequence of the gene encoding the elongase enzyme; 2) constructing a vector comprising said nucleotide sequence; and 3) introducing said vector into a host cell under time and conditions sufficient for the production of the elongase enzyme.

The present invention also encompasses a method of producing polyunsaturated fatty acids comprising exposing an acid to the enzyme such that the elongase converts the acid to a polyunsaturated fatty acid. For example, when LA is exposed to a Δ9-elongase enzyme, it is converted to EDA. EDA may then be exposed to, for example, Δ8 -desaturase which converts the EDA to DGLA. The DGLA then may be converted to AA by exposing the DGLA to, for example, Δ5-desaturase. Thus, Δ9-elongase may be used in the production of polyunsaturated fatty acids which may be used, in turn, for particular beneficial purposes, or may be used in the production of other PUFAs.

Uses of the Δ9-Elongase Gene

As noted above, the isolated elongase gene and the elongase enzyme encoded thereby have many uses. For example, the gene and corresponding enzyme may be used indirectly or directly in the production of polyunsaturated fatty acids, for example, Δ9-elongase may be used in the production of EDA, ETrA, DGLA, ETA, AA, EPA, ω3-docosapentaenoic acid, ω6-docosapentaenoic acid, ADA and/or DHA. ("Directly" is meant to encompass the situation where the enzyme directly converts the acid to another acid, the latter of which is utilized in a composition (e.g., the conversion of LA to EDA). "Indirectly" is meant to encompass the situation where an acid is converted to another acid (i.e., a pathway intermediate) by the enzyme (e.g., LA to EDA) and then the latter acid is converted to another acid by use of a non-elongase enzyme (e.g., EDA to DGLA by, for example, Δ8-desaturase). These polyunsaturated fatty acids (i.e., those produced either directly or indirectly by activity of the elongase enzyme) may be added to, for example, nutritional compositions, pharmaceutical compositions, cosmetics, and animal feeds, all of which are encompassed by the present invention. These uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic functions.

The nutritional composition of the present invention comprises at least one oil or acid produced directly or indirectly by use of the elongase gene, in accordance with the present invention, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions. Nutritional compositions of particular interest include but are not limited to those utilized for enteral and parenteral supplementation for infants, specialty infant formulas, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio). An oil or acid produce in accordance with the present invention may be add to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substance boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight percent of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as AA, from about 0.22% to about 0.67% as DGLA, and from about 0.27% to about 1.04% as GLA. Thus, fatty acids such as AA, EPA and/or DHA, produced in accordance with the present invention, can be used to alter, for example, the composition of infant formulas in order to better replicate the PUPA content of human breast milk or to alter the presence of PUFAs normally found in a non-human mammal's milk. In particular, a composition for use in a pharmacologic or food supplement, particularly a breast milk substitute or supplement, will preferably comprise one or more of AA, EPA, DGLA, and DHA. More preferably, the oil will comprise from about 0.3 to 30% AA, and from about 0.2 to 30% DGLA.

Parenteral nutritional compositions comprising from about 2 to about 30 weight percent fatty acids calculated as triglycerides are encompassed by the present invention. Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of AA and DGLA can be adapted for a particular given end use. When formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as EDA and DGLA to AA can be used to precisely control the PUFA ratios. For example, a 5% to 10% conversion rate of DGLA to AA can be used to produce an AA to DGLA ratio of about 1:19, whereas a conversion rate of about 75% TO 80% can be used to produce an AA to DGLA ratio of about 6:1. Therefore, whether in a cell culture system or in a host animal, regulating the timing, extent and specificity of elongase expression, as well as the expression of desaturases and other elongases, can be used to modulate PUFA levels and ratios. The PUFAs/ acids produced in accordance with the present invention (e.g., AA and EPA) may then be combined with other PUFAs/acids (e.g., DGLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the acids and/or resulting oils produced using the elongase gene described herein, in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectable, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition ran also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% AA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit for, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., *Am. J. Clin. Nutr.* Vol. 57 (Suppl.) 732S-737S). Altered fatty acid metabolism and composition have been demonstrated in diabetic animals.

Furthermore, the compositions of the present invention, comprising PUFAs produced either directly or indirectly through the use of the elongase enzyme, may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., *Adv. Exp. Med. Biol.* Vol. 83, p. 85-101, 1976), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal or aquaculture feed supplements, animal feed substitutes, animal vitamins or in animal topical ointments.

The present invention may be illustrated by the use of the following non-limiting examples:

EXAMPLE 1

Cloning of Full Length Elongase Like cDNA from Thraustochytrid sp. BICC 7087

A cDNA library was constructed at Incyte Corporation (Wilmington, Del.) from the fungus Thraustochytrid sp. BICC 7087 (BP0091). cDNA synthesis was initiated using an oligo (dT) primer containing EcoRI restriction site in the first strand synthesis reaction. Following the second strand synthesis, double stranded cDNA was blunted, ligated to NotI adapters, digested with NotI and EcoRI, size selected and cloned into the NotI (5' of the cDNA insert) and EcoRI (3' of the cDNA insert) sites of pBluescript (KS+) vector. The library ligation mix was diluted 10 fold and transformed into *Escherichia coli* DH10B competent cells according to Incyte's transformation protocol. The library was stored in glycerol stock after recovering the transformants. The titer appeared to be 1.14 millions primary clones/total ligation mix.

Around 5000 clones were then sequenced using T3 primer and the sequence was generated from the 5' end of each clone (EST). The sequenced templates that passed Incyte's sequencing QC specification (overall success rate of 85% reads) were then processed through Incyte's Bioinformatics Sequence Editing Pipeline and assembled into contigs. Assembled sequences were then annotated using BLAST2 against the appropriate GenBank divisions and using FASTX against GenPept.

A clone, designated '660R1,' was obtained from sequencing of clones from Thraustochytrid sp. BICC 7087 (T7087) cDNA library. This molecule shared 30.6% amino acid sequence identity with the mouse elongase MELO4 and 35.3% amino acid sequence identity with Thraustochytrid sp. BICC elongase TELO1 (FIG. 4).

Figure 5:
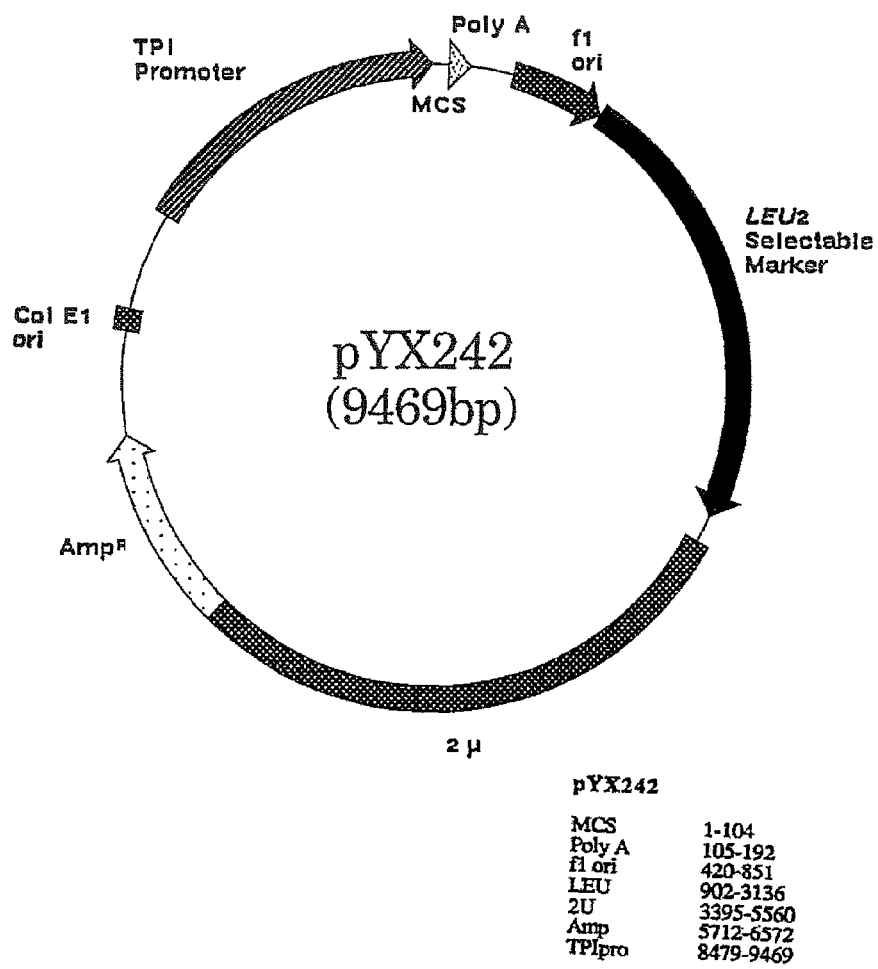
FIG. 5 illustrates the physical map of the constitutive yeast expression vector, pYX242, used for the cloning of Δ9-elongase gene (SEQ ID NO:1) for the production of encoded elongase enzyme in yeast.

To isolate the full-length gene, the 660R1 EST clone was used as a template for PCR reaction with 10 pmol of the 5' primer RO1206 (5'-AGA AGA CC<u>ATGG</u> GGG ACC TCG AAA GAT AC-3' SEQ ID NO:3) and 10 pmol of the 3' primer RO1207 (5'-AGA GCT AAG C<u>TTA</u>GG CAG ATT TTG TCT TGG GC-3' SEQ ID NO:4). RO1206 contains NcoI restriction site (CCATGG) and the start codon ATG (underlined) while RO1207 contains HindIII restriction site (AAGCTT) and the stop codon (underlined). PCR was carried out in a 50 μl volume containing: 1 μl of 660R1 cDNA, 0.2 μM dNTP mix, 10 pmole of each primer, 5 μl of 10×buffer, 1.5 μl of 50 mM MgSO$_4$, and 0.5 U of cDNA Polymerase. Thermocycler conditions in Perkin Elmer 9600 were as follows: 94° C. for 3 min, then 30 cycles of 94° C. for 45 sec., 55° C. for 30 sec., and 68° C. for 2 min. The PCR amplified mixture was run on a gel, an amplified molecule of approximately 810 bp was gel purified, the termini of the molecule were digested with NcoI and HindIII, and the molecule was cloned into pYX242 (NcoI/HindIII) (FIG. 5). The recombinant plasmid was designated as pRAT-5A1. The nucleotide sequence (SEQ ID NO: 1) and the deduced amino acid sequence (SEQ ID NO: 2) are shown in FIG. 2 and FIG. 3, respectively.

Plasmid DNA pRAT-5A1 was deposited with the American Type Culture Collection, 10801 University Boulevard, Manassas, Va. 20110-2209, on Nov. 14, 2006, under the terms of the Budapest Treaty, and was accorded deposit number ATCC PTA-8001.

EXAMPLE 2

Expression of Thraustochytrid sp. BICC 7087 Elongase cDNA in Baker's Yeast

The construct pRAT-5A1 was transformed into *Saccharomyces cerevisiae* 334 (Hoveland et al., Gene. 1989; 83:57-64) and screened for elongase activity. *Saccharomyces cerevisiae* 334 containing pYX242 vector alone was used as a control. The cultures were grown for 48 hours at 24° C., in selective minimal media lacking leucine (Ausubel et al., Short Protocols in Molecular Biology. 1995. pp. 4.8-4.9), in the presence of 50 μM of LA, ALA or EPA. For LA and ALA elongation, EDA and ETrA respectively were the predicted elongated products showing Δ9-elongase activity. After 48 hours of incubation, cells were harvested by centrifugation. The cell pellet was washed once with sterile distilled/deionized water. Total yeast lipids were then extracted and the fatty acid analysis was performed as described in Knutzon et al. (J. Biol. Chem. 273:29360-29366 (1998)). Briefly, the rinsed cell pellet was extracted with 30 ml of chloroform/methanol (2:1, v/v). Exactly 17.216 μg of triheptadecanoin was added to the lipid extract as the internal standard. The extracted lipids were derivatized with 2 mL 14% boron triflouride in methanol as described by Yamasaki et al (JAOCS 76: 933-938, 1999). Fatty acid methyl esters were then analyzed by gas chromatography (GC) using a flame-ionization detector and a fused-silica capillary column (Omegawax; 30 mm×0.32 mm, i.d., film thickness 0.25 μm, Supelco, Bellefonte, Pa.). The identity of various metabolites was confirmed by gas chromatography using GLC reference standard #461 (Nu Chek Prep). The enzyme activity was indicated by the conversion of substrates to products, based on the ratio of [product]/[products+ substrate]×100%. The levels of substrate and its metabolic products taken up by the yeast were also calculated, based on the fatty acid distribution as percentage of total fatty acids.

The lipid profiles of the recombinant yeast culture containing pRAT-5A-1 construct indicated that there was a 4.9% conversion of LA to EDA, 21% conversion of ALA to ETrA and 2.2% conversion of EPA to ω3-docosapentaenoic acid over pYX242 control (FIG. 6). Elongation of LA and ALA to EDA and EtrA, respectively, is by the action of Δ9-elongase via the alternate delta 8 pathway (FIG. 1). From the results, pRAT-5A1 appears to possess Δ9-elongation activity preferring ALA (21% conversion) as a substrate over LA (5% conversion) under experimental conditions in yeast. Thus, this fungal sequence, pRAT-5A1 and its encoded protein, possesses Δ9-elongase activity. In addition, pRAT-5A1-encoded protein was also found to elongate 16:1n-7 substrate to 18:1n-7 in yeast (data not shown).

EXAMPLE 3

Sequence Comparison Between pRAT-5A1 and other Known Elongases

The sequence analysis package of Vector NTI Suite 9 (Invitrogen Corporation, Carlsbad, Calif.) was used to compare the pRAT-5A1 with known protein sequences. The nucleotide sequence of pRAT-5A1 open reading frame was first translated into amino acid sequence. This amino acid sequence of pRAT-5A1 was then used in the sequence homology comparison with other published Δ9-elongase sequence from different organisms. Sequence alignment was performed using Vector NTI software and the percentile of positive alignment was determined. The amino acid sequence of pRAT-5A1 had 32.0% identity with *Danio rerio* Δ9-elongase (FIG. 7), 33.9% with *Isochrysis galbana* Δ9-elongase (FIG. 8) and 35.4% with *Pavlova salina* Δ9-elongase (FIG. 9). The functional activity of all these Δ9-elongases have been established and published. The amino acid sequence of pRAT-5A1 was also used for performing BLAST searches on the NCBI-Genbank database to determine other sequence homologies. A sequence homology of 85.8% was found with a recently published sequence from *Thraustochytrium* sp. FJN-10 (Genbank Accession # ABC18314) (FIG. 10), however no functional characterization of the protein encoded by this sequence has been demonstrated.

EXAMPLE 4

Identification of Amino Acid Residues in pRAT-5A1 that are Important Determinants of Elongase Activity Amino acid sequence comparison of known fatty acid elongase proteins that are involved in PUFA biosynthesis has revealed certain shared structural characteristics. There is a highly conserved histidine-box motif, containing three histidine residues, HXXHH, embedded in the fourth membrane spanning region, and the presence of five hydrophobic stretches predicted to be membrane-spanning regions. The histidine-box region is predicted to be essential for elongase activity since it is highly conserved across the PUFA-elongase family (Leonard et al., (2004) *Prog Lipid Res.* 43(1):36-54). pRAT-5A1 shares these same sequence characteristics with other PUFA-elongases, with the histidine box (HVLHH) located between amino acid position $H_{154}$ and $H_{158}$. In addition, another motif that appears to be shared across PUFA-elongating enzymes in the 'HXYMY' motif (FIG. 11). It is not known if this HXYMY motif is essential for enzymatic activity.

To determine if the Histidine-box (including some flanking conserved regions) and the 'HXYMY' motifs are important determinants for elongase enzymatic activity, site-directed mutagenesis was carried out on the pRAT-5A1 gene. Two separate sets of mutations were generated within the pRAT-5A1 sequence, one within the Histidine-box motif (including some conserved flanking regions) (pRAT-5A1 mutant 1), and one at the HXYMY motif (pRAT-5A1 mutant 2). A comparison of the proteins encoded by 'pRAT-5A1 mutant 1' (SEQ ID NO:5) and 'pRAT-5A1 mutant 2 (SEQ ID NO:6) is depicted in FIG. 11. pRAT-5A1 mutant 1 shares 98.5% amino acid sequence identity with pRAT-5A1, and pRAT-5A1 mutant 2 shares 98.9% amino acid sequence identity with pRAT-5A1. The resulting changes in the encoded amino acid sequence of the mutants are as indicated below:

| pRAT1 | | |
|---|---|---|
| | pRAT-5A1 mutant 1 | |
| $\underline{F}_{152}\underline{L}_{153}$ H V L $\underline{H}_{157}\underline{H}_{158}$ | → | $\underline{A}_{152}\underline{P}_{153}$ H V L $\underline{D}_{157}\underline{D}_{158}$ |
| | pRAT-5A1 mutant 2 | |
| $\underline{H}_{187}$ T V $\underline{M}_{190}$ $\underline{Y}_{191}$ | → | $\underline{D}_{187}$ T V $\underline{A}_{190}$ $\underline{A}_{191}$ |

To generate the 'pRAT-5A1 mutant 1, the pRAT-5A1 gene (cloned into pYX242) was used as a template for PCR amplification. A 623 bp sequence (Fragment A) containing the 5' end of the gene along with part of the 5' flanking vector sequence was PCR amplified used the following primers:

```
pYX242 vector FP
                                              (SEQ ID NO:7)
5'-AGT GAA CTT GCA ACA TTT AC-3' pRAT5A1 mutant 1 RP
                                              (SEQ ID NO:8)
5'-AAG CCA AAA GGT GGT TGC GTC GTC CAA GAC ATG CGG

CGC ACG CAA CTT GTT GCC CTT G-3'
```

The remaining 603 bp (Fragment B) of the pRAT-5A1 gene along with some of the 3' flanking vector was PCR amplified used the following primers:

```
pYX242 vector RP
                                              (SEQ ID NO:9)
5'-CGA CGG CCA GTG AAT TGT-3' pRAT5A1 mutant 1 FP
                                              (SEQ ID NO:10)
5'-CAA GGG CAA CAA GTT GCG TGC GCC GCA TGT CTT GGA

CGA CGC AAC CAC CTT TTG GCT T-3'
```

The PCR reaction mix consisted of 200 ng template DNA, 200 µM (final concentration) dNTPs, 1×PWO polymerase buffer (10 mM Tris-Cl pH 8.8, 25 mM KCl, 5 mM $(NH4)_2SO_4$ and 2 mM $Mg_2SO_4$), 100 pmoles each of forward and reverse primers and 1 unit of PWO DNA polymerase (Roche). PCR amplification conditions were as follows: An initial denaturation at 94° C./2 min followed by 30 cycles of [Denaturation at 94° C./30 sec; Annealing at 58° C./30 sec; Extension at 72° C./30 sec]. This was followed by extension at 72° C./2 min and finally held at 4° C. indefinitely.

To generate the full-length 'pRAT-5A1 mutant 1', overlapping PCR was carried out using Fragment A and Fragment B as a template along with vector primers 'pYX242 vector FP' (SEQ ID NO: 7) and pYX242 vector RP (SEQ ID NO:9). PCR amplification conditions were as described above. This generated a 1.2 kb DNA fragment containing the 'pRAT-5A1 mutant 1' gene and vector flanking regions with the NcoI/HindIII restriction sites. The full-length 'pRAT-5A1 mutant 1' gene was then cloned into pYX242 vector at the NcoI/HindIII site.

Similarly, to generate the 'pRAT-5A1 mutant 2' gene, the pRAT-5A1 gene (cloned into pYX242) was used as a template for PCR amplification. A 720 bp sequence (Fragment A) containing the 5' end of the gene along with part of the 5' flanking vector sequence was PCR amplified used the following primers:

```
pYX242 vector FP
                                              (SEQ ID NO:7)
5'-AGT GAA CTT GCA ACA TTT AC-3' pRAT5A1 mutant 2 RP
                                              (SEQ ID NO:11)
5'-AGG GAC GAA AGT AGT GCG CCG CCG CGA CCG TGT CAA

TAA AAG CAT TCA CGG CG-3'
```

The remaining 502 bp (Fragment B) of the pRAT-5A1 gene along with some of the 3' flanking vector was PCR amplified used the following primers:

```
pYX242 vector RP
                                              (SEQ ID NO:9)
5' CGA CGG CCA GTG AAT TGT 3' pRAT5A1 mutant 2 FP
                                              (SEQ ID NO:12)
5' CGC CGT GAA TGC TTT TAT TGA CAC GGT CGC GGC GGC

GCA CTA CTT TCG TCC CT 3'
```

PCR amplification and generation of the full-length 'pRAT-5A1 mutant 2' gene was carried out using the same technique described for the isolation of pRAT-5A1 mutant 1. The two mutant clones thus obtained were sequenced to verify that the appropriate mutations were created in the pRAT-5A1 sequence. The two mutant clones were then transformed into *Saccharomyces cerevisiae* SC334 and screened for Δ9-elongase activity as described in Example 2. Fatty acid substrates tested were linoleic acid (LA, 18:2 n-6) and alpha-linolenic acid (ALA, 18:3 n-3). Fatty acid extraction and analysis was carried out as described in Example 2.

The lipid profiles of the recombinant yeast culture expressing the 'pRAT-5A1 mutant 1' or 'pRAT-5A1 mutant 2' indicated that there was a considerable decrease in activity as compared to the activity of the original pRAT-5A1 clone (FIG. 12). With both mutants, the elongation activity decreased by greater than 50% (FIG. 12). 'pRAT-5A1 mutant 2' appeared to lose greater activity in comparison to that of 'pRAT-5A1 mutant 1' (FIG. 12). These studies confirm the importance of the Histidine-box region for enzyme functionality. In addition, here it has been demonstrated that the region flanking the Histidine-box (FLHXXHH) may also be important for enzyme functionality. These studies demonstrate, for the first time, the importance of the 'HXYMY' motif in elongation activity. All these regions may be directly involved in the catalytic activity of the enzyme and/or may play an essential role in stabilizing the protein structure.

Two additional sequence variants of pRAT-5A1 were analyzed for Δ9-elongase activity. These sequence variants, designated pRAT-5A11 and pRAT-5B6, were isolated during the process of PCR amplification of the full-length gene of pRAT-5A1. The random mutations in these sequences were probably PCR-induced errors caused by certain DNA polymerases that have low proof-reading activity (enzyme specificity). The encoded amino acid sequences of pRAT-5A11 (SEQ ID 15), pRAT5B6 (SEQ ID 16) and pRAT-5A1 (SEQ ID 2) are depicted in FIG. 13. Amino acid residues that differ from the pRAT-5A1 encoded protein are underlined and highlighted in FIG. 13. pRAT-5A11 shares 98.5% amino acid sequence identity with pRAT-5A1, and pRAT-5B6 shares 99.6% amino acid sequence identity with pRAT-5A1.

Yeast expression studies with the pRAT-5A11-encoded protein revealed that pRAT-5A11 had much lower Δ9-elongase activity than pRAT-5A1 (60% decrease in enzymatic activity), in the conversion of LA to EDA and ALA to ETrA (data not shown). This indicates that the four amino acid residues that differ between pRAT-5A11 and pRAT-5A1 are important determinants for enzymatic activity. These four amino acid residues include $I_{39}$, $V_{49}$, $L_{72}$ and $P_{118}$ as seen in pRAT-5A1 (FIG. 13).

Expression of pRAT-5B6 in yeast did not reveal any differences in enzymatic activity as compared to expression of pRAT-5A1. This indicates that this single amino acid mutation (D101→N101) can be accommodated without much change to the enzyme activity of pRAT-5A1.

EXAMPLE 5

Seed-Specific Expression of pRAT-5A1 in Arabidopsis

The pRAT-5A1 gene cloned into a plant expression vector p0308-DsRed, to test for activity in plants. For generation of the construct, pRAT-5A1 was PCR amplified with the Phusion polymerase (New England Biolabs) according to conditions specified by the manufacturer. The primers used for this PCR included:

```
Sense primer
                                        (SEQ ID NO:13)
5'-TATGAATTCAAAATGGGGACCTCGAAAGATAC-3'

Antisense primer
                                        (SEQ ID NO:14)
5'-TATACTGGAGTTAGGCAGATTTTGTCTTGGGC-3'.
```

Figure 14:
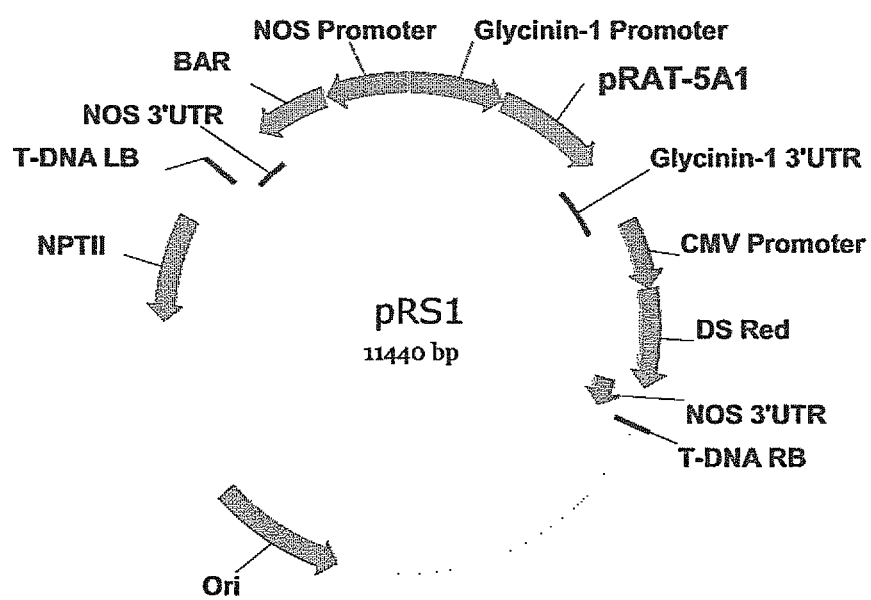
FIG. 14 illustrates the physical map of the plant expression vector, pRS1, used for the cloning of the pRAT-5A1 encoded protein and for expression studies in plant seeds.

The PCR amplified gene was then digested with restriction enzymes EcoRI and XhoI, and the resulting product was linked on its 5'-end to the seed-specific glycinin-1 promoter from soybean and on its 3'-end to the glycinin-1 3' untranslated region in the binary vector p0308-DsRed to generate plasmid pRS1 (FIG. 14). The glycinin-1 regulatory elements have been previously described by Nielsen et al., (1989) Plant Cell 1:313-328. This vector also contains a Ds-Red transgene under control of the cassava mosaic virus promoter for selection of transgenic seeds by fluorescence and a kanamycin resistance marker for bacterial selection. The elongase gene was sequenced in the binary vector to confirm the absence of any mutations resulting from PCR amplification.

pRS1 was introduced into Agrobacterium tumefaciens strain C58 MP90 by electroporation. Kanamycin-resistant agrobacterium was then used for transformation of Arabidopsis thaliana ecotype Col-0 by the floral dip method (Clough et al., (1998) Plant J 16:735-743). For these experiments, a fad3/fae1 mutant of Arabidopsis was used that contains low levels of α-linolenic acid and very-long chain fatty acids (≥C20) but elevated levels of linoleic acid in its seed oil (Cahoon et al., (2006) Phytochemistry 67:1166-1176). This genetic background approximates the fatty acid profile of seed oils from crops such as safflower and low linolenic acid soybean. Transgenic seeds obtained from the agrobacterium-dipped Arabidopsis plants were identified by fluorescence of the DsRed marker protein using the methodology described by Pidkowich et al. (Pidkowich et al., (2007) Proc Natl Acad Sci USA 104:4742-4747). Single transgenic and nontransgenic control seeds were subjected to direct transesterication of the constituent lipids, including triacylglycerols, by use of the protocol described by Cahoon and Shanklin (Cahoon et al., (2000) Proc Natl Acad Sci USA 97:12350-12355). Fatty acid methyl esters obtained from the single seeds were analyzed by gas chromatography with flame ionization detection by use of an Agilent 6890 gas chromatograph fitted with an INNOWax column (30 m length×0.25 mm inner diameter) and oven temperature programming from 185° C. (1 min hold) to 230° C. (2 min hold) at 7° C./min. Component fatty acid methyl esters were identified based on their retention times relative to fatty acid methyl esters of known identity from seeds of wild-type Arabidopsis thaliana Col-0 and by structural analysis using gas chromatography-mass spectrometry.

Shown in FIG. 15 are the fatty acid compositions of single seeds from five independent transformation events with the pRS1 construct, which contains the pRAT-5A1 gene. Also shown are the fatty acid compositions of non-transgenic control seeds. As seen in FIG. 15, the transgenic lines that express the pRAT-5A1-encoded enzyme actively elongate Linoleic acid (LA, 18:2n-6) substrate to produce ω6-eicosadienoic acid (EDA, 20:2n-6) (FIG. 15). Line 3 shows the highest activity with a 26% conversion of 18:2n-6 substrate to 20:2n-6 product. This activity is not detected in the non-transgenic lines that do not express pRAT-5A1. Thus the pRAT-5A1-encoded enzyme will be useful for the production of transgenic oils containing arachidonic acid (ARA, 20:4 n6), eicosapentaenoic acid (EPA, 20:5 n-3) and or docosahexaenoic acid (DHA, 20:6 n-3), by virtue of its functionality in the alternate pathway (Δ9-elongase-Δ8 desaturase pathway) leading to biosynthesis of ARA, EPA and DHA (FIG. 1).

Nutritional Compositions

The PUFAs described in the Detailed Description may be utilized in various nutritional supplements, infant formulations, nutritional substitutes and other nutritional solutions.

I. Infant Formulations

A. Isomil® Soy Formula with Iron:

Usage: As a beverage for infants, children and adults with an allergy or sensitivity to cows milk. A feeding for patients with disorders for which lactose should be avoided: including lactase deficiency, lactose intolerance and galactosemia.

Features:

Soy protein isolate to avoid symptoms of cow's-milk-protein allergy or sensitivity.

Lactose-free formulation to avoid lactose-associated diarrhea.

Low osmolality (200 mOs/kg water).

Dual carbohydrates (corn syrup and sucrose) designed to maximize absorption and minimize risk of malabsorption.

Ingredients: 43.2% Corn Syrup Solids, 14.6% Soy Protein Isolate, 11.5% High Oleic Safflower Oil, 10.3% Sugar (Sucrose), 8.4% Soy Oil, 8.1% Coconut Oil: Less Than 2% Of: Calcium Phosphate, Potassium Citrate, Potassium Chloride, Magnesium Chloride, Sodium Chloride, Ascorbic Acid, Choline Chloride, L-Methionine, Taurine, Ascorbyl Palmitate, Ferrous Sulfate, m-Inositol, Mixed Tocopherols, Zinc Sulfate, d-Alpha-Tocopheryl Acetate, L-Carnitine, Niacinamide, Calcium Pantothenate, Cupric Sulfate, Thiamine Chloride Hydrochloride, Vitamin A Palmitate, Riboflavin, Pyridoxine Hydrochloride, Folic Acid, Potassium Iodide, Potassium Hydroxide, Phylloquinone, Biotin, Sodium Selenate, Beta-Carotene, Vitamin D3 and Cyanocobalamin.

B. Isomil® DF Soy Formula for Diarrhea:

Usage: For the dietary management of diarrhea in infants and toddlers.

Features:

First infant formula to contain added dietary fiber from soy fiber specifically for diarrhea management.

Clinically shown to reduce the duration of loose, watery stools during mild to severe diarrhea in infants.

Lactose-free formulation to avoid lactose-associated diarrhea.

Low osmolality (240 mOsm/kg water) to reduce the risk of osmotic diarrhea.

Ingredients: 85.7% water, 4.8% corn syrup, 2.6% sugar (sucrose), 2.1% soy oil, 2.0% soy protein isolate, 1.4% coconut oil, 0.77% soy fiber, calcium citrate, potassium citrate, calcium phosphate, potassium phosphate, potassium chloride, mono and diglycerides, soy lecithin, magnesium chloride, carrageenan, ascorbic acid, L-methionine, sodium chloride, choline chloride, taurine, ferrous sulfate, m-inositol, d-alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® Advance® Soy Formula with Iron:

Usage: As a beverage for infants, children and adults with an allergy or sensitivity to cows milk. A feeding for patients with disorders for which lactose should be avoided: including lactase deficiency, lactose intolerance and galactosemia.

Features:

Contains DHA and ARA, two nutrients found in breast milk important for mental and visual development.

Soy protein isolate to avoid symptoms of cow's-milk-protein allergy or sensitivity.

Lactose-free formulation to avoid lactose-associated diarrhea.

Low osmolality (200 mOs/kg water).

Dual carbohydrates (corn syrup and sucrose) designed to maximize absorption and minimize risk of malabsorption.

Ingredients: 43.2% Corn Syrup Solids, 14.6% Soy Protein Isolate, 11.5% High Oleic Safflower Oil, 10.3% Sugar (Sucrose), 8.4% Soy Oil, 7.7% Coconut Oil, *C. Cohnii* Oil, *M. Alpina* Oil, Calcium Phosphate, Potassium Citrate, Potassium Chloride, Magnesium Chloride, Sodium Chloride, Ascorbic Acid, Choline Chloride, L-Methionine, Taurine, Ascorbyl Palmitate, Ferrous Sulfate, m-Inositol, Mixed Tocopherols, Zinc Sulfate, d-Alpha-Tocopheryl Acetate, L-Carnitine, Niacinamide, Calcium Pantothenate, Cupric Sulfate, Thiamine Chloride Hydrochloride, Vitamin A Palmitate, Riboflavin, Pyridoxine Hydrochloride, Folic Acid, Potassium Iodide, Potassium Hydroxide, Phylloquinone, Biotin, Sodium Selenate, Beta-Carotene, Vitamin D3 and Cyanocobalamin.

D. Isomil® Advance® 20 Soy Formula with Iron Ready to Feed, 20 Cal/Fl Oz.:

Usage: When a soy feeding is desired.

Ingredients: 85.9% water, 6.7% corn syrup, 1.9% soy protein isolate, 1.4% high oleic safflower oil, 1.3% sugar (sucrose), 1.1% soy oil, 1.0% coconut oil, *C. cohnii* oil, *m. alpina* oil, calcium citrate, calcium phosphate, potassium citrate, potassium chloride, mono- and diglycerides, soy lecithin, carrageenan, abscorbic acid, L-methionine, magnesium chloride, potassium phosphate, sodium chloride, choline chloride, taurine, ferrous sulfate, m-inositol, d-alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. Similac® Infant Formula:

Usage: When an infant formula is needed: if the decision is made to discontinue breastfeeding before age 1 year, if a supplement to breastfeeding is needed or as a routine feeding if breastfeeding is not adopted. Powder, Concentrated Liquid and Ready To Feed forms.

Ingredients: Water, nonfat milk, lactose, high oleic safflower oil, soy oil, coconut oil, whey protein concentrate, potassium citrate, calcium carbonate, abscorbic acid, soy lecithin, monoglycerides, carrageenan, potassium chloride, magnesium chloride, ferrous sulfate, choline chloride, choline bitartrate, taurine, m-inositol, zinc sulfate, niacinamide, d-alpha-tocopheryl acetate, calcium pantothenate, l-carnitine, vitamin A palmitate, riboflavin, cupric sulfate, thiamine chloride hydrochloride, pyridoxine hydrochloride, folic acid, manganese sulfate, phylloquinone, biotin, beta-carotene, sodium selenite, vitamin D3, cyanocobalamin, calcium phosphate, potassium phosphate, sodium chloride, potassium hydroxide and nucleotides (adenosine 5'-monophosphate, cytidine 5'-monophosphate, disodium guanosine 5'-monophosphate, disodium uridine 5'-monophosphate).

F. Similac® Advance® Infant Formula with Iron:

Usage: For use as a supplement of alternative to breast-feeding. Powder, Concentrated Liquid and Ready To Feed forms.

Ingredients: Water, nonfat milk, lactose, high oleic safflower oil, soy oil, coconut oil, whey protein concentrate, *C. cohnii* oil, *M. alpina* oil, potassium citrate, calcium carbonate, abscorbic acid, soy lecithin, monoglycerides, carrageenan, potassium chloride, magnesium chloride, ferrous sulfate, choline chloride, choline bitartrate, taurine, m-inositol, zinc sulfate, niacinamide, d-alpha-tocopheryl acetate, calcium pantothenate, l-carnitine, vitamin A palmitate, riboflavin, cupric sulfate, thiamine chloride hydrochloride, pyridoxine hydrochloride, folic acid, manganese sulfate, phylloquinone, biotin, beta-carotene, sodium selenite, vitamin D35 cyanocobalamin, calcium phosphate, potassium phosphate, sodium chloride, potassium hydroxide and nucleotides (adenosine 5'-monophosphate, cytidine 5'-monophosphate, disodium guanosine 5'-monophosphate, disodium uridine 5'-monophosphate).

G. Similac® NeoSure® Advance® Infant Formula with Iron:

Usage: A special formula for conditions such as prematurity.

Features:

Well absorbed fat blend that contains 25% added medium-chain triglycerides(MCTs).

Higher levels of protein, vitamins and minerals per 100 Cal than standard term formula.

More calcium and phosphorus than standard term formula.

Ingredients: nonfat milk, corn syrup solids, lactose, soy oil, high oleic safflower oil, whey protein concentrate, medium chain triglycerides, coconut oil, *c. cohnii* oil, *m. alpina* oil, potassium citrate, calcium phosphate, m-inositol, ascorbic acid, magnesium chloride, calcium carbonate, taurine, ferrous sulfate, choline bitartrate, choline chloride, ascorbyl palmitate, L-carnitine, potassium chloride, sodium chloride, zinc sulfate, mixed tocopherols, d-alpha-tocopheryl acetate, sodium citrate, niacinamide, potassium phosphate, calcium pantothenate, cupric sulfate, vitamin A palmitate, thiamine chloride hydrochloride, riboflavin, pyridoxine hydrochloride, beta carotene, folic acid, manganese sulfate, phylloquinone, biotin, sodium selenite, vitamin D3, cyanocobalamin and nucleotides (adenosine 5'-monophosphate, cytidine 5'-monophosphate, disodium guanosine 5'-monophosphate, disodium uridine 5'-monophosphate).

H. Similac Natural Care Advance Low-Iron Human Milk Fortifier Ready to Use, 24 Cal/fl oz.:

Usage: Designed to be mixed with human milk or to be fed alternatively with human milk to low-birth-weight infants.

Ingredients: Water, nonfat milk, corn syrup solids, lactose, medium-chain triglycerides, whey protein concentrate, soy oil, coconut oil, *C. cohnii* oil, *M. alpina* oil, calcium phosphate, potassium citrate, ascorbic acid, calcium carbonate, magnesium chloride, soy lecithin, mono and diglycerides, m-inositol, sodium citrate, carrageenan, choline bitartrate, taurine, choline chloride, niacinamide, d-alpha tocopheryl acetate, L-carnitine, zinc sulfate, potassium chloride, potassium phosphate dibasic, calcium pantothenate, ferrous sulfate, cupric sulfate, riboflavin, vitamin A palmitate, thiamine chloride hydrochloride, pyridoxine hydrochloride, biotin, folic acid, beta carotene, manganese sulfate, phylloquinone, vitamin D3, sodium selenite, cyanocobalamin and nucleotides (adenosine 5'-monophosphate, cytidine 5'-monophosphate, disodium guanosine 5'-monophosphate, disodium uridine 5'-monophosphate).

Various PUFAs of this invention can be substituted and/or added to the infant formulae described above and to other infant formulae known to those in the art.

II. Nutritional Formulations

A. ENSURE®

Usage: Rich, creamy-tasting ENSURE provides a source of complete, balanced nutrition for supplemental use between or with meals and for interim sole-source feeding. ENSURE can benefit people who are at nutrition risk, experiencing involuntary weight loss, recovering from illness or surgery, or on modified or low-residue diets. For oral feeding. For interim sole-source feeding. Retail product for supplemental oral nutrition Ingredients: Water, Sugar (Sucrose), Corn Maltodextrin, Milk Protein Isolate, Soy Oil, Corn Oil, Canola Oil, Soy Protein Concentrate, Potassium Citrate, Natural & Artificial Flavor, Magnesium Phosphate, Sodium Citrate, Soy Lecithin, Calcium Phosphate, Magnesium Chloride, Salt (Sodium Chloride), Choline Chloride, Carrageenan, Ascorbic Acid, dl-Alpha-Tocopheryl Acetate, Ferrous Sulfate, Zinc Sulfate, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Sodium Selenate, Phylloquinone, Potassium Iodide, Vitamin D3 and Cyanocobalamin.

B. ENSURE® HIGH PROTEIN:

Usage: ENSURE HIGH PROTEIN is useful for people who need extra protein and nutrition in their diet ENSURE HIGH PROTEIN is suitable for use by people recovering from general surgery or hip or other bone fractures, and is a good source of nutrition for those who have or are at risk for pressure ulcers. For supplemental oral nutrition.

Ingredients: Water, Sugar (Sucrose), Corn Maltodextrin, Calcium and Sodium Caseinates, Soy Oil, Soy Protein Isolate, Corn Oil, Potassium Citrate, Canola Oil, Calcium Phosphate, Sodium Citrate, Magnesium Chloride, Magnesium Phosphate, Artificial Flavor, Salt (Sodium Chloride), Soy Lecithin, Choline Chloride, Ascorbic Acid, Carrageenan, Zinc Sulfate, dl-Alpha-Tocopheryl Acetate, Ferrous Sulfate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

C. ENSURE PLUS®

Usage: ENSURE PLUS is a source of complete, balanced nutrition that provides concentrated calories and protein to help patients gain or maintain healthy weight. It can be used with or between meals or as a meal replacement. For oral feeding. For interim sole-source feeding. For patients with fluid restrictions or require volume-limited feedings Features:

650 mg omega-3 fatty acid ALA (40% of 1.6 g RDI) to support heart health.

Excellent source of 24 essential vitamins and minerals.

Source of antioxidants selenium and vitamins C and E to strengthen the immune system.

Low in cholesterol.

Kosher.

Gluten-free.

Lactose-free.

Ingredients: Vanilla: Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

D. ENSURE® POWDER:

Usage: ENSURE® POWDER (reconstituted with water) is complete, balanced nutrition for supplemental use with or between meals. It may benefit people who are on modified diets, at nutrition risk, experiencing involuntary weight loss, recovering from illness or surgery, or on low-residue diets.

Features:
Convenient, easy to mix
Low residue
Lactose and gluten free

Ingredients: Corn Syrup, Corn Maltodextrin, Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate, Potassium Chloride, Soy Lecithin, Ascorbic Acid, Choline Chloride, Zinc Sulfate, dl-Alpha-Tocopheryl Acetate, Niacinamide, Ferrous Sulfate, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenate, Phylloquinone, Cyanocobalamin and Vitamin D3.

E. ENSURE® PUDDING

Usage: ENSURE PUDDING is a nutritious alternative to other snacks or desserts. It provides complete, balanced nutrition in a delicious easy-to-eat form. It is appropriate for those who are underweight or undernourished, or are on a fluid-restricted or volume-limited diet. For people on consistency-modified diets (eg, soft, pureed, or full liquid). For people with swallowing impairments. For supplemental oral nutrition Features:
Good source of 24 essential vitamins and minerals.
Convenient-needs no refrigeration.
Gluten-free.
Includes 1 g or FOS per serving (FOS are prebiotics that stimulate the growth of beneficial bacterial in the colon).

Ingredients:
Vanilla: Water, Sugar (Sucrose), Modified Corn Starch, Partially Hydrogenated Soybean Oil, Milk Protein Concentrate, Nonfat Milk, Fructooligosaccharides, Magnesium Sulfate, Potassium Phosphate, Sodium Phosphate, Sodium Stearoyl Lactylate, Artificial Flavor, Sodium Ascorbate, Zinc Sulfate, dl-Alpha-Tocopheryl Acetate, Ferrous Sulfate, Niacinamide, Manganese Sulfate, Calcium Pantothenate, FD&C Yellow #5 & #6, Cupric Sulfate, Thiamine Chloride Hydrochloride, Pyridoxine Hydrochloride, Vitamin A Palmitate, Riboflavin, Folic Acid, Chromium Chloride, Biotin, Sodium Molybdate, Potassium Iodide, Sodium Selenate, Phylloquinone, Vitamin D3 and Cyanocobalamin.

F. ENSURE® WITH FIBER:

Usage: ENSURE FIBER is a source of complete, balanced nutrition for people who can benefit from increased dietary fiber and nutrients. The fiber blend with FOS, a prebiotic, helps maintain digestive-tract health. ENSURE FIBER is suitable for people who do not require a low-residue diet. It can be fed orally or by tube. ENSURE FIBER can benefit people who are on modified diets, are at nutritional risk, are experiencing involuntary weight loss, or are recovering from illness or surgery. For oral feeding. For interim sole-source feeding.

Features:
Includes 1 g of FOS/8 fl oz. FOS fiber (nondigetible carbohydrate) helps promote natural defenses in the colon.
Excellent source of 24 essential vitamins and minerals.
Provides 2.8 g total dietary fiber per 8-fl-oz serving.
Lactose and gluten-free.

Ingredients:
Vanilla: Water; Corn Maltodextrin, Sugar (Sucrose), Sodium and Calcium Caseinates, Soy Oil, Soy Protein Isolate, Corn Oil, Oat Fiber, Fructooligosaccharides, Canola Oil, Soy Fiber, Calcium Phosphate, Magnesium Chloride, Potassium Citrate, Cellulose Gel, Soy Lecithin, Potassium Phosphate, Sodium Citrate, Natural and Artificial Flavors, Choline Chloride, Magnesium Phosphate, Ascorbic Acid, Cellulose Gum, Potassium Chloride, Carrageenan, Ferrous Sulfate, di-Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

The various nutritional supplements described above and known to others of skill in the art can be substituted and/or supplemented with the PUFAs produced in accordance with the present invention.

G. Oxepa™ Nutritional Product

OXEPA is clinically shown to modulate the inflammatory response in critically ill, mechanically ventilated patients. It is appropriate for patients who have sepsis, SIRS (systemic inflammatory response syndrome), ALI (acute lung injury), or ARDS (acute respiratory distress syndrome). For tube feeding. For sole-source nutrition Caloric Distribution:

The distribution of Calories in Oxepa is shown in Table A.

TABLE A

| Caloric Distribution of Oxepa | | | |
|---|---|---|---|
| | per 8 fl oz. | per liter | % of Cal |
| Calories | 355 | 1,500 | — |
| Fat (g) | 22.2 | 93.8 | 55.2 |
| Carbohydrate (g) | 25 | 105.3 | 28.1 |
| Protein (g) | 14.8 | 62.5 | 16.7 |
| Water (g) | 186 | 785 | — |

Ingredients: Water, Calcium and Sodium Caseinates, Sugar (Sucrose), Canola Oil, Medium Chain Triglycerides, Sardine Oil, Borage Oil, Magnesium Chloride, Calcium Phosphate, Soy Lecithin, Potassium Citrate, Sodium Citrate, Ascorbic Acid, Potassium Phosphate, Natural and Artificial Flavor, Choline Chloride, Taurine, d-Alpha-Tocopheryl Acetate, L-Carnitine, Salt (Sodium Chloride), Gellan Gum, Zinc Sulfate, Ferrous Sulfate, Niacinamide, Calcium Pantothenate, Manganese Sulfate, Cupric Sulfate, Thiamine Chloride Hydrochloride, Pyridoxine Hydrochloride, Riboflavin, Beta-Carotene, Vitamin A Palmitate, Folic Acid, Chromium Chloride, Biotin, Sodium Molybdate, Potassium Iodide, Sodium Selenate, Phylloquinone, Vitamin D3 and Cyanocobalamin.

The various fatty acid components of Oxepa™ nutritional product can be substituted and/or supplemented with the PUFAs produced in accordance with this invention.

The invention claimed is:

1. A method of producing an elongase comprising the steps of:
 a) isolating a nucleotide sequence comprising SEQ ID NO:1;
 b) constructing a vector comprising: i) said isolated nucleotide sequence operably linked to ii) a regulatory sequence;
 c) introducing said vector into a host cell for a time and under conditions sufficient for expression of said elongase.

2. The method of claim 1 wherein said host cell is selected from the group consisting of a eukaryotic cell and a prokaryotic cell.

3. The method of claim 2 wherein said prokaryotic cell is selected from the group consisting of *Escherichia coli*, cyanobacteria and *Bacillus subtilis*.

4. The method of claim 2 wherein said eukaryotic cell is selected from the group consisting of a mammalian cell, an insect cell, a plant cell and a fungal cell.

5. The method of claim 4 wherein said fungal cell is selected from the group consisting of *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp.

6. The method of claim 5 wherein said fungal cell is a yeast cell selected from the group consisting of *Saccharomyces* spp., *Candida* spp., *Hansenula* spp. And *Pichia* spp.

7. The method of claim 6 wherein said yeast cell is *Saccharomyces cerevisiae*.

8. A vector comprising: a) cDNA comprising a nucleotide sequence comprising SEQ ID NO:1 operably linked to b) a regulatory sequence.

9. An isolated host cell comprising said vector of claim 8.

10. The isolated host cell of claim 9, wherein said host cell is selected from the group consisting of a eukaryotic cell and a prokaryotic cell.

11. The isolated host cell of claim 10, wherein said prokaryotic cell is selected from the group consisting of *Escherichia coli*, cyanobacteria and *Bacillus subtilis*.

12. The isolated host cell of claim 10, wherein said eukaryotic cell is selected from the group consisting of a mammalian cell, an insect cell, a plant cell and a fungal cell.

13. The isolated host cell of claim 12, wherein said fungal cell is selected from the group consisting of *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp.

14. The isolated host cell of claim 13 wherein said fungal cell is a yeast cell selected from the group consisting of *Saccharomyces* spp., *Candida* spp., *Hansenula* spp. And *Pichia* spp.

15. The isolated host cell of claim 14, wherein said host cell is *Saccharomyces cerevisiae*.

16. An isolated mammalian cell comprising said vector of claim 8, wherein expression of said nucleotide sequence of said vector results in production of altered levels of eicosadienoic acid (EDA) and/or eicosatrienoic acid (ETrA), when said cell is grown in a culture media comprising at least one fatty acid selected from the group consisting of linoleic acid (LA) and α-linolenic acid (ALA).

17. A plant cell comprising said vector of claim 8, wherein expression of said nucleotide sequence of said vector results in production of at least one polyunsaturated fatty acid by said plant cell.

18. The plant cell of claim 17 wherein said polyunsaturated fatty acid is selected from the group consisting of eicosadienoic acid (EDA), α-linolenic acid (ALA), and eicosatrienoic acid (EtrA).

19. A transgenic plant or plant tissue comprising said vector of claim 8, wherein expression of said nucleotide sequence of said vector results in production of at least one polyunsaturated fatty acid in said transgenic plant or plant tissue wherein said polyunsaturated fatty acid is selected from the group consisting of eicosadienoic acid (EDA), α-linolenic acid (ALA), and eicosatrienoic acid (ETrA).

* * * * *